(12) United States Patent
Hall et al.

(10) Patent No.: US 8,759,311 B2
(45) Date of Patent: Jun. 24, 2014

(54) USE OF SIRNA TARGETTING SIPA1L1 FOR THE REDUCTION OF ADIPOGENESIS

(75) Inventors: Diana Hall, Lausanne (CH); Maria Jimenez, Chavennes-pres-Renens (CH); Carine Poussin, Evian-les-Bains (FR); Bernard Thorens, Epalinges (CH)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/498,951

(22) PCT Filed: Oct. 1, 2010

(86) PCT No.: PCT/IB2010/054436
§ 371 (c)(1),
(2), (4) Date: Sep. 27, 2012

(87) PCT Pub. No.: WO2011/039729
PCT Pub. Date: Apr. 7, 2011

(65) Prior Publication Data
US 2013/0018083 A1    Jan. 17, 2013

(30) Foreign Application Priority Data
Oct. 1, 2009   (EP) .................................... 09305929

(51) Int. Cl.
*C12N 15/11*   (2006.01)
*C12Q 1/68*    (2006.01)

(52) U.S. Cl.
USPC ........................................ 514/44 A; 435/6.1

(58) Field of Classification Search
None
See application file for complete search history.

(56) References Cited

U.S. PATENT DOCUMENTS 5,795,716 A     8/1998  Livache et al.
2003/0064477 A1  4/2003  Band et al.

FOREIGN PATENT DOCUMENTS

WO   WO 01/82948 A2   11/2001

OTHER PUBLICATIONS

Richter et al, The EphA4 Receptor Regulates Neuronal Morphology through SPAR-Mediated Inactivation of Rap GTPases, Dec. 2007, The Journal of Neuroscience, 27(51):14205-14215.*
International Search Report WO2011/039729 A1 dated Apr. 7, 2011.
Banerjee et al., The Kruppel-like Factor KLF2 Inhibits Peroxisome Proliferator activated Receptor-y Expression and Adipogenesis, J. of Biol. Chem , vol. 278, No. 4, Jan. 24, 2003, pp. 2581-2584.
Bhattacharyya et al., RNA bulges and the helical periodcity of double-stranded RNA, Natue, vol. 343, Feb. 1, 1990, pp. 484-487.
Chen et al., Krox20 stimulates adipogenesis via C/EBP Beta-dependent and -independent mechanisms, Cell Metabolism, vol. 1, Feb. 2005, pp. 93-106.
Collins et al., Genetic vulnerability to diet-induced obesity in the C57BL/6J mouse: physiological and molecular characteristics, Physiology & Behavior, vol. 81, 2004, pp. 243-248.
De Fourmestraux et al., Transcript Profiling Suggests That Differential Metabolic Adaptation of Mice to a High Fat Diet Is Associated with Changes in Liver to Muscle Lipid Fluxes, J of Biol. Chem., Vol. 279, No. 49, Dec. 3, 2004, pp. 50743-50753.
Gray et al., The Kruppel-like Factor KLF15 Regulates the insulin-sensitive Glucose Transporter GLUT4, J. of Biol. Chem. vol. 277, No. 37, Sep. 13, 2002, pp. 34322-34328.
Jimenez et al., Critical Role for Ebf1 and Ebf2 and Ebf2 in the Adipogenic Transcriptional Cascada, Molecular and Cellular Biology, vol. 27, No. 2. Jan. 2007, pp. 743-757.
Jordan et al., Transfection of adherent and suspended cells by calcium phosphate. Methods, vol. 33, 2004, pp. 136-143.
Kang et al., Wnt Signaling Stimulates Osteoblastogenesis of Mesenchymal Precursors by Suppressing CCAAT/Enhancer-binding Protein and Peroxisome Proliferator-activated Receptor y. J. of Biol. Chem. vol. 282, No. 19, May 11, 2007, pp. 14515-14524.
Poirier et al., The anti-obesity effet of rimonabant is associated with improved lipid profile, Diabetes, Obesity and Metabolism, vol. 7, 2005, pp. 65-72.
Rosen et al., Adipocyte differentiation from the inside out, Nature Rev. Molecular Cell Biology, vol. 7, Dec. 2006, pp. 885-896.
Rosen et al., Adipocytes as regulators of energy balance and glucose homeostasis, Nature, vol. 44, Dec. 14, 2006, pp. 847-853.
Rosen et al., C/EBPalpha induces adipogenesis through PPARg: a unified pathway, Genes & Development, vol. 16, 2002, pp. 22-26.
Rosen et al., Transcriptional regulation of adipogenesis, Genes Dev. vol. 14, No. 11, 2000, pp. 1293-1307.
Sadhu et al., in Vitro Synthesis of Double Stranded RNA and Measurement of Thermal Stability: Effect of Base Composition. Formamide and Ionic Strength, Biochemistry International, vol. 14, No. 6, Jun. 1987, pp. 1015-1022.
Tsai et al., A Wnt-CKIvarepsilon-Rap1 pathway regulates gastrulation by modulating SIPA1L1, a Rap GTPase activating protein, Developmental Cell, vol. 12, Mar. 2007, pp. 335-347.

* cited by examiner

*Primary Examiner* — Tracy Vivlemore
*Assistant Examiner* — Kate Poliakova-Georgantas
(74) *Attorney, Agent, or Firm* — Lathrop & Gage LLP

(57) ABSTRACT

The present invention concerns Sipa1l1, a new target involved in adipogenesis modulation. Using a siRNA approach, the inventors demonstrated that decrease in Sipa1l1 activity in preadipocytes and adipose tissue induces a decrease in adipogenesis. Thus, the present invention relates to modulators of Sipa1l1 activity as well as screening test for identification of modulators of the activity of this target, and their use, especially in pharmaceutical composition, to modulate adipogenesis and thus treat obesity and related disorders.

9 Claims, 5 Drawing Sheets

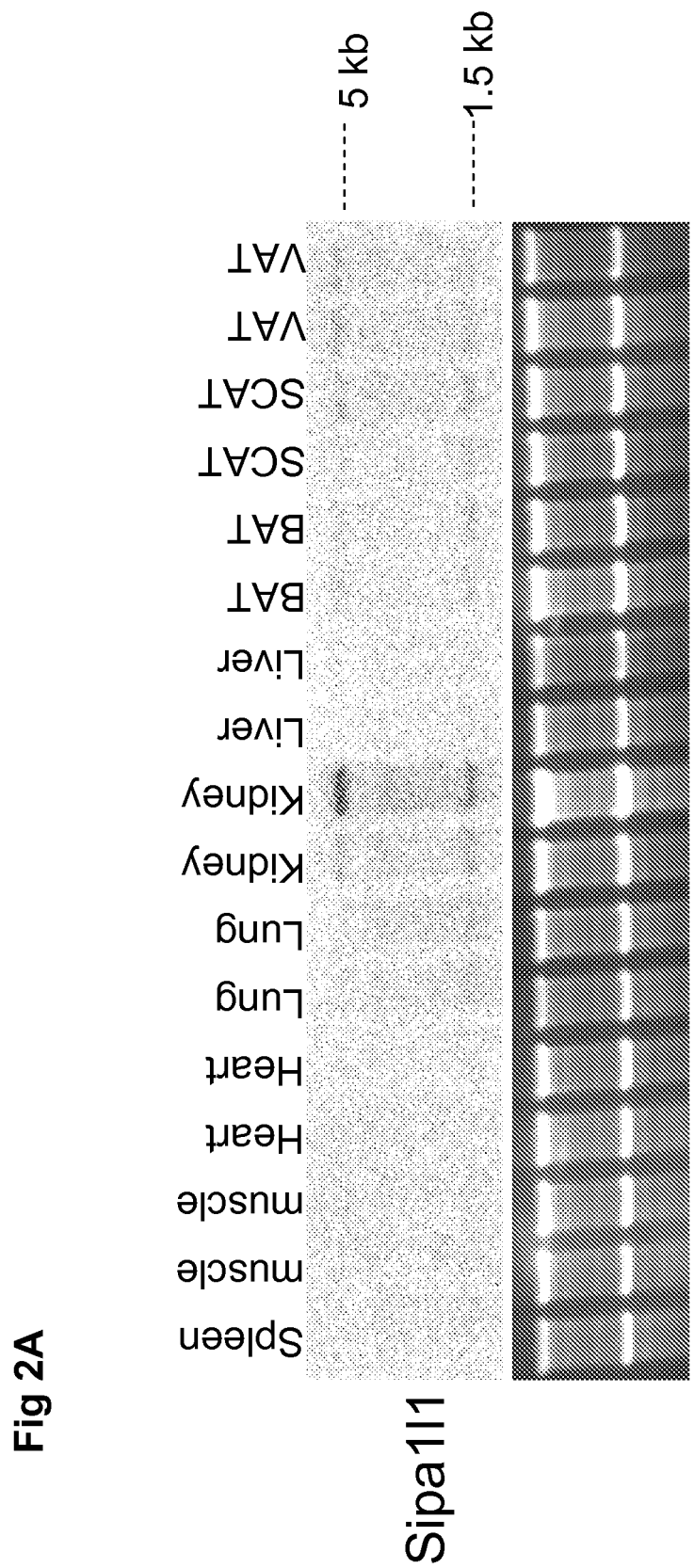

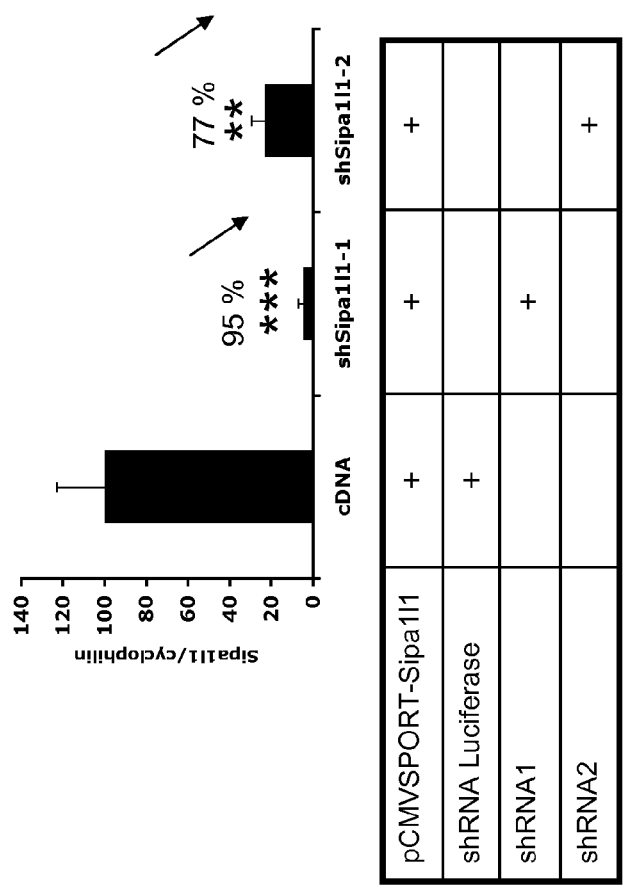
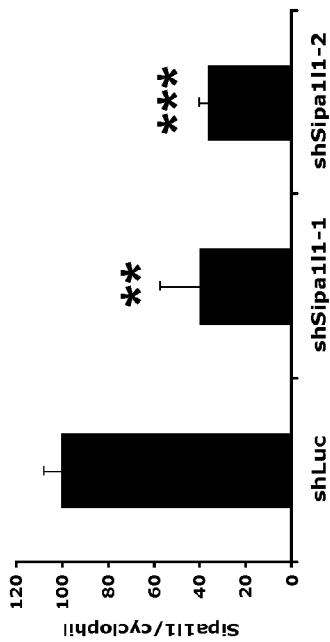
Fig 3A
Fig 3B

SEQUENCE LISTING

<160> NUMBER OF SEQ ID NOS: 19

<210> SEQ ID NO 1
<211> LENGTH: 6003
<212> TYPE: DNA
<213> ORGANISM: Mus musculus
<220> FEATURE:
<221> NAME/KEY: CDS
<222> LOCATION: (428)..(5776)

<400> SEQUENCE: 1

```
gaatggaata ctgtcagtgg actaaggtca tatgtcatta gtgtggacgc tgctgtctta      60
agtctgtggc catggcacca gaacacaggg aagcgtggga ttctggtgac cacagagccc     120
cagtgatgca agctctactc agtcttaggg actgaaggaa gcctgctgtt agagtgaggc     180
acagggactg aaggaagcct gctgttagag tgaggcacag gactgttgt ggattacaat     240 gtttggaaga tctgggttct ctgtcgtctg caaacaaggc atcatttaac cttttaaatg     300
aaaaggctta agatctcaac accactgctg tattttctgg aagccattct ctaaagcaga     360
agtgcatatt taaaacgcaa acatggtgat cctttctgca gggatttaag tgatcgcttt     420 ttacatc atg acc agt ttg aag cgg tcg cag acc gaa aga cct gtc acc      469
        Met Thr Ser Leu Lys Arg Ser Gln Thr Glu Arg Pro Val Thr
        1               5                   10 gct gac aga gcc tct gtt gtc agc aca gat ggc gcc ccc aaa gtc cac      517
Ala Asp Arg Ala Ser Val Val Ser Thr Asp Gly Ala Pro Lys Val His
15                  20                  25                  30 acc gat gac ttc tac atg cgt cgc ttc cgc tct cag aat ggc agc cta      565
Thr Asp Asp Phe Tyr Met Arg Arg Phe Arg Ser Gln Asn Gly Ser Leu
                35                  40                  45 gga tca tca gtc atg gct gca gtg ggg ccc cct cga agt gaa ggc cct      613
Gly Ser Ser Val Met Ala Ala Val Gly Pro Pro Arg Ser Glu Gly Pro
            50                  55                  60 cac cat atc acc tca acc ccc ggg gtc ccc aag atg ggg gtt agg gca      661
His His Ile Thr Ser Thr Pro Gly Val Pro Lys Met Gly Val Arg Ala
        65                  70                  75 aga ata gca gat tgg cct ccg aga aag gaa aat gta aaa gaa tcc agc      709
Arg Ile Ala Asp Trp Pro Pro Arg Lys Glu Asn Val Lys Glu Ser Ser
    80                  85                  90 cgt tca agc cag gaa ata gaa acc tca agt tgc ctt gag agc ctg tcc      757
Arg Ser Ser Gln Glu Ile Glu Thr Ser Ser Cys Leu Glu Ser Leu Ser
95                  100                 105                 110 tcc aaa ggc agt cct gtg agt cag ggg agt tct gtt agc ctc aat tcc      805
Ser Lys Gly Ser Pro Val Ser Gln Gly Ser Ser Val Ser Leu Asn Ser
                115                 120                 125 aat gac tca gcc atg ctg aag agc ata cag aac acc ctg aag aac aag      853
Asn Asp Ser Ala Met Leu Lys Ser Ile Gln Asn Thr Leu Lys Asn Lys
            130                 135                 140 aca ggg cca gcg gag agc atg gac tcc aga ttc ctc atg cct gaa gcc      901
Thr Gly Pro Ala Glu Ser Met Asp Ser Arg Phe Leu Met Pro Glu Ala
        145                 150                 155 tac ccc agt tcc ccc agg aaa gcc ctt cgc aga att cgg cag cgc agc      949
Tyr Pro Ser Ser Pro Arg Lys Ala Leu Arg Arg Ile Arg Gln Arg Ser
    160                 165                 170 aac agt gat atc acc ata agt gag ctt gat gtg gat agc ttc gat gaa      997
Asn Ser Asp Ile Thr Ile Ser Glu Leu Asp Val Asp Ser Phe Asp Glu
175                 180                 185                 190
```

```
tgt atc tcc cca acc tac aag tcg ggg cca tca ttg cac agg gaa tat    1045
Cys Ile Ser Pro Thr Tyr Lys Ser Gly Pro Ser Leu His Arg Glu Tyr
                195                 200                 205 ggc agc aca tct tca atc gac aag cag gga aca tcc gga gac agc ttc    1093
Gly Ser Thr Ser Ser Ile Asp Lys Gln Gly Thr Ser Gly Asp Ser Phe
            210                 215                 220 ttc gat ttg tta aag ggc tat aaa gat gac aga tct gac cga ggt cca    1141
Phe Asp Leu Leu Lys Gly Tyr Lys Asp Asp Arg Ser Asp Arg Gly Pro
        225                 230                 235 act cca acc aaa ctc agt gac ttc ctc atc act ggt ggg ggc aag ggt    1189
Thr Pro Thr Lys Leu Ser Asp Phe Leu Ile Thr Gly Gly Gly Lys Gly
    240                 245                 250 tct ggt ttc tcc ttg gat gtg atc gat ggc ccc atc tca cag aga gag    1237
Ser Gly Phe Ser Leu Asp Val Ile Asp Gly Pro Ile Ser Gln Arg Glu
255                 260                 265                 270 aac ctc agg ctt ttc aag gaa agg gaa aaa cca ctc aag cga cgc tct    1285
Asn Leu Arg Leu Phe Lys Glu Arg Glu Lys Pro Leu Lys Arg Arg Ser
                275                 280                 285 aag tct gag act gga gac tcg tcc att ttt cgt aaa ttg cgc aat gcc    1333
Lys Ser Glu Thr Gly Asp Ser Ser Ile Phe Arg Lys Leu Arg Asn Ala
            290                 295                 300 aaa ggt gaa gaa ctc ggg aaa tca tca gac ctt gaa gac aac aga tca    1381
Lys Gly Glu Glu Leu Gly Lys Ser Ser Asp Leu Glu Asp Asn Arg Ser
        305                 310                 315 gaa gat tct gtg agg ccc tgg aca tgt cca aag tgc ttt gcc cac tat    1429
Glu Asp Ser Val Arg Pro Trp Thr Cys Pro Lys Cys Phe Ala His Tyr
    320                 325                 330 gat gtc cag agc ata ttg ttt gac ttg aat gaa gcc att atg aac aga    1477
Asp Val Gln Ser Ile Leu Phe Asp Leu Asn Glu Ala Ile Met Asn Arg
335                 340                 345                 350 cat aat gtg att aag agg aga aac acc aca aca gga gct tcg gcg gct    1525
His Asn Val Ile Lys Arg Arg Asn Thr Thr Thr Gly Ala Ser Ala Ala
                355                 360                 365 gcg gtg gca tcc ttg gtc tcc gga cct ctg tct cac tca gcc agc ttc    1573
Ala Val Ala Ser Leu Val Ser Gly Pro Leu Ser His Ser Ala Ser Phe
            370                 375                 380 agc tct ccc atg ggc agc aca gag gac ctc aac tcc aaa gga agc ctt    1621
Ser Ser Pro Met Gly Ser Thr Glu Asp Leu Asn Ser Lys Gly Ser Leu
        385                 390                 395 ggc atg gac cag gga gat gac aag agc aat gaa ctc gtc atg agc tgt    1669
Gly Met Asp Gln Gly Asp Asp Lys Ser Asn Glu Leu Val Met Ser Cys
    400                 405                 410 ccg tat ttt cgg aat gag att ggg gga gaa ggt gag agg aag atc agc    1717
Pro Tyr Phe Arg Asn Glu Ile Gly Gly Glu Gly Glu Arg Lys Ile Ser
415                 420                 425                 430 ctg tcc aag tcg aat tct ggc tca ttt agt ggg tgt gag agc aca tcc    1765
Leu Ser Lys Ser Asn Ser Gly Ser Phe Ser Gly Cys Glu Ser Thr Ser
                435                 440                 445 ttt gag tct gcc ctc agc tct cac tgc acc aac gcg ggc gtg gca gtt    1813
Phe Glu Ser Ala Leu Ser Ser His Cys Thr Asn Ala Gly Val Ala Val
            450                 455                 460 ctc gaa gtg ccc aag gaa agc ttg atg ctg cat ctg gac agg gtg aaa    1861
Leu Glu Val Pro Lys Glu Ser Leu Met Leu His Leu Asp Arg Val Lys
        465                 470                 475 agg tac acc gtg gaa cac gtg gat ctt ggc gca tac tat tac agg aag    1909
Arg Tyr Thr Val Glu His Val Asp Leu Gly Ala Tyr Tyr Tyr Arg Lys
    480                 485                 490 ttc ttc tac cag aag gaa cac tgg aac tat ttt ggg gct gat gag aac    1957
Phe Phe Tyr Gln Lys Glu His Trp Asn Tyr Phe Gly Ala Asp Glu Asn
```

```
                495                 500                 505                 510
ctc ggt cca gtg gct gtg agc att cga agg gaa aaa cca gaa gac atg       2005
Leu Gly Pro Val Ala Val Ser Ile Arg Arg Glu Lys Pro Glu Asp Met
                    515                 520                 525 aag gaa aac gga tct cca tac aac tac cga ata ata ttc agg act agt       2053
Lys Glu Asn Gly Ser Pro Tyr Asn Tyr Arg Ile Ile Phe Arg Thr Ser
            530                 535                 540 gag ctc atg acg ctg agg ggg tct gtc ctg gag gat gcc att ccc tcc       2101
Glu Leu Met Thr Leu Arg Gly Ser Val Leu Glu Asp Ala Ile Pro Ser
        545                 550                 555 acg gcc aag cac tcg aca gcc agg gga ttg cct ctg aaa gag gtg ctg       2149
Thr Ala Lys His Ser Thr Ala Arg Gly Leu Pro Leu Lys Glu Val Leu
    560                 565                 570 gaa cac gtg atc cca gag ctc aac gtg cag tgc ctg cgc ttg gcc ttc       2197
Glu His Val Ile Pro Glu Leu Asn Val Gln Cys Leu Arg Leu Ala Phe
575                 580                 585                 590 aac aca ccc aaa gtc aca gag cag ctc atg aaa ctg gac gag caa ggg       2245
Asn Thr Pro Lys Val Thr Glu Gln Leu Met Lys Leu Asp Glu Gln Gly
                595                 600                 605 ctg aac tat cag cag aaa gta ggc atc atg tac tgc aaa gca ggc cag       2293
Leu Asn Tyr Gln Gln Lys Val Gly Ile Met Tyr Cys Lys Ala Gly Gln
            610                 615                 620 agc acg gag gag gag atg tac aac aac gag tct gca ggc cca gcc ttt       2341
Ser Thr Glu Glu Glu Met Tyr Asn Asn Glu Ser Ala Gly Pro Ala Phe
        625                 630                 635 gag gag ttc ctt cag ctg ctg ggg gaa cga gtc cgg cta aaa gga ttc       2389
Glu Glu Phe Leu Gln Leu Leu Gly Glu Arg Val Arg Leu Lys Gly Phe
    640                 645                 650 gag aag tat cgt gcg cag ctt gac acc aaa act gac tcc act gga acc       2437
Glu Lys Tyr Arg Ala Gln Leu Asp Thr Lys Thr Asp Ser Thr Gly Thr
655                 660                 665                 670 cac tct ctg tac aca acc tac aaa gac tat gag ata atg ttc cac gtc       2485
His Ser Leu Tyr Thr Thr Tyr Lys Asp Tyr Glu Ile Met Phe His Val
                675                 680                 685 tcc acc atg ctg ccc tac aca cct aac aac aag caa cag ctc ctg agg       2533
Ser Thr Met Leu Pro Tyr Thr Pro Asn Asn Lys Gln Gln Leu Leu Arg
            690                 695                 700 aag cgg cac att ggg aat gac att gtg aca ata gtt ttc caa gag cct       2581
Lys Arg His Ile Gly Asn Asp Ile Val Thr Ile Val Phe Gln Glu Pro
        705                 710                 715 gga gca caa cca ttc agc ccg aaa aac atc cgg tct cac ttt cag cat       2629
Gly Ala Gln Pro Phe Ser Pro Lys Asn Ile Arg Ser His Phe Gln His
    720                 725                 730 gtt ttt gtc att gtc cgg gct cac aac cct tgc act gag agt gtc tgt       2677
Val Phe Val Ile Val Arg Ala His Asn Pro Cys Thr Glu Ser Val Cys
735                 740                 745                 750 tac agt gtg gca gtc acc agg tcc aga gat gta cct tct ttt gga cct       2725
Tyr Ser Val Ala Val Thr Arg Ser Arg Asp Val Pro Ser Phe Gly Pro
                755                 760                 765 ccc atc cct aaa ggg gtc acc ttc ccc aag tca aat gtg ttc agg gac       2773
Pro Ile Pro Lys Gly Val Thr Phe Pro Lys Ser Asn Val Phe Arg Asp
            770                 775                 780 ttc ctt ttg gcc aaa gtg ata aat gca gaa aat gct gct cat aaa tca       2821
Phe Leu Leu Ala Lys Val Ile Asn Ala Glu Asn Ala Ala His Lys Ser
        785                 790                 795 gag aag ttc cgg gcc atg gcg aca agg acc cgc cag gaa tac ctg aaa       2869
Glu Lys Phe Arg Ala Met Ala Thr Arg Thr Arg Gln Glu Tyr Leu Lys
    800                 805                 810 gat ctg gca gaa aag aat gtc acc aac aca cct att gac cct tct ggc       2917
Asp Leu Ala Glu Lys Asn Val Thr Asn Thr Pro Ile Asp Pro Ser Gly
```

|     |     |     |     |     |     |     |     |     |     |     |     |     |     |     |      |
|-----|-----|-----|-----|-----|-----|-----|-----|-----|-----|-----|-----|-----|-----|-----|------|
| Asp | Leu | Ala | Glu | Lys | Asn | Val | Thr | Asn | Thr | Pro | Ile | Asp | Pro | Ser | Gly  |
| 815 |     |     |     | 820 |     |     |     | 825 |     |     |     |     |     | 830 |      |

```
aag ttt cca ttt att tct ctg gcc tcc aag aag aag gaa aag tct aag     2965
Lys Phe Pro Phe Ile Ser Leu Ala Ser Lys Lys Lys Glu Lys Ser Lys
            835                 840                 845 cct tat cca gga gct gag ctc agt aac atg ggg gcc att gtg tgg gct     3013
Pro Tyr Pro Gly Ala Glu Leu Ser Asn Met Gly Ala Ile Val Trp Ala
        850                 855                 860 gtc cgg gcc aaa gac tac aac aag gcc atg gag ttc gac tgc ctc ctt     3061
Val Arg Ala Lys Asp Tyr Asn Lys Ala Met Glu Phe Asp Cys Leu Leu
        865                 870                 875 ggg atc tcc agc gag ttc atc gtc ctc att gag cag gag aca aag agt     3109
Gly Ile Ser Ser Glu Phe Ile Val Leu Ile Glu Gln Glu Thr Lys Ser
    880                 885                 890 gtg gct ttc aat tgc tcc tgc aga gat gtc ata ggg tgg act tcc agc     3157
Val Ala Phe Asn Cys Ser Cys Arg Asp Val Ile Gly Trp Thr Ser Ser
895                 900                 905                 910 gac acc agc ctc aaa atc ttc tat gag cgg gga gaa tgt gtg tcg gtg     3205
Asp Thr Ser Leu Lys Ile Phe Tyr Glu Arg Gly Glu Cys Val Ser Val
                915                 920                 925 gag agc ttc att agc ggt gaa gat atc aaa gaa att gtc aga agg ctg     3253
Glu Ser Phe Ile Ser Gly Glu Asp Ile Lys Glu Ile Val Arg Arg Leu
            930                 935                 940 cag ttt gtt tca aaa ggt tgt gaa tct gtg gaa atg act ctg cga aga     3301
Gln Phe Val Ser Lys Gly Cys Glu Ser Val Glu Met Thr Leu Arg Arg
        945                 950                 955 aat ggg ctg ggg cag ctt ggc ttc cat gtc aac tat gag ggc att gtg     3349
Asn Gly Leu Gly Gln Leu Gly Phe His Val Asn Tyr Glu Gly Ile Val
    960                 965                 970 gcg gat gta gaa ccc tac ggc tac gca tgg caa gca ggg ctg agg cag     3397
Ala Asp Val Glu Pro Tyr Gly Tyr Ala Trp Gln Ala Gly Leu Arg Gln
975                 980                 985                 990 ggc agc cgc ctg gtg gag atc tgc aag gta gca gtg gcc acc ctg agc     3445
Gly Ser Arg Leu Val Glu Ile Cys Lys Val Ala Val Ala Thr Leu Ser
                995                 1000                1005 cat gaa cag atg atc gat ctc ttg aga aca tca gtc aca gtg aag         3490
His Glu Gln Met Ile Asp Leu Leu Arg Thr Ser Val Thr Val Lys
                1010                1015                1020 gtt gtc att atc cct ccc cat gac gac tgc acc cca cgg agg agt         3535
Val Val Ile Ile Pro Pro His Asp Asp Cys Thr Pro Arg Arg Ser
                1025                1030                1035 tgc tca gaa acc tac cgc atg cca gtg atg gag tac cag atg aat         3580
Cys Ser Glu Thr Tyr Arg Met Pro Val Met Glu Tyr Gln Met Asn
                1040                1045                1050 gaa ggc att tcc tac gag ttc aag ttt ccc ttc cgg aat aat aac         3625
Glu Gly Ile Ser Tyr Glu Phe Lys Phe Pro Phe Arg Asn Asn Asn
                1055                1060                1065 aaa tgg cag cgg aat gcc agc aag ggt gct cat tcg ccc cag gtt         3670
Lys Trp Gln Arg Asn Ala Ser Lys Gly Ala His Ser Pro Gln Val
                1070                1075                1080 cca tct cag ctg cag agt ccc atg acc tca cga ctg aat gct ggg         3715
Pro Ser Gln Leu Gln Ser Pro Met Thr Ser Arg Leu Asn Ala Gly
                1085                1090                1095 aag gga gat ggg aaa atg ccc cct cca gaa aga gct gcc aac atc         3760
Lys Gly Asp Gly Lys Met Pro Pro Pro Glu Arg Ala Ala Asn Ile
                1100                1105                1110 cct cga agc atc tcc agt gac ggg cgc cca ctg gaa agg agg ctg         3805
Pro Arg Ser Ile Ser Ser Asp Gly Arg Pro Leu Glu Arg Arg Leu
                1115                1120                1125
```

```
tct cct ggt tcg gac atc tat gtg aca gtc tca tcc atg gct ttg       3850
Ser Pro Gly Ser Asp Ile Tyr Val Thr Val Ser Ser Met Ala Leu
            1130            1135                1140 gcg aga tcc cag tgc cgt aac tct ccc agc aac ttg tct tcg tcc       3895
Ala Arg Ser Gln Cys Arg Asn Ser Pro Ser Asn Leu Ser Ser Ser
            1145            1150                1155 agt gag act ggc tct gga ggt ggt acc tac aga caa aaa tcc atg       3940
Ser Glu Thr Gly Ser Gly Gly Gly Thr Tyr Arg Gln Lys Ser Met
            1160            1165                1170 ccc gaa ggg ttt ggg gtg agc cga aga tcc cca gct tcc atc gac       3985
Pro Glu Gly Phe Gly Val Ser Arg Arg Ser Pro Ala Ser Ile Asp
            1175            1180                1185 agg cag aac acc cag tcg gat ata agt ggc agt gga aaa tcc act       4030
Arg Gln Asn Thr Gln Ser Asp Ile Ser Gly Ser Gly Lys Ser Thr
            1190            1195                1200 ccc agc tgg cag aga agt gag gac agc ctt gcc gac cag atg gag       4075
Pro Ser Trp Gln Arg Ser Glu Asp Ser Leu Ala Asp Gln Met Glu
            1205            1210                1215 ccg acg tgc cat ctc cca gca gta tcg aag gta ctg cct gct ttc       4120
Pro Thr Cys His Leu Pro Ala Val Ser Lys Val Leu Pro Ala Phe
            1220            1225                1230 cga gag agc ccc agt ggg aga ttg atg cgg cag gat cca gtg gtt       4165
Arg Glu Ser Pro Ser Gly Arg Leu Met Arg Gln Asp Pro Val Val
            1235            1240                1245 cac ttg tct cca aac aaa caa ggc cat tct gac agc cac tac tcc       4210
His Leu Ser Pro Asn Lys Gln Gly His Ser Asp Ser His Tyr Ser
            1250            1255                1260 agc cac tcc agc agc aac acg ctc tcc agc aac gcc tcg agt gca       4255
Ser His Ser Ser Ser Asn Thr Leu Ser Ser Asn Ala Ser Ser Ala
            1265            1270                1275 cac agt gac gag aag tgg tac gat ggg gac cgc acg gag tcc gac       4300
His Ser Asp Glu Lys Trp Tyr Asp Gly Asp Arg Thr Glu Ser Asp
            1280            1285                1290 ctc aac agc tac aac tac cta cag ggc acg tct gcc gac agc ggg       4345
Leu Asn Ser Tyr Asn Tyr Leu Gln Gly Thr Ser Ala Asp Ser Gly
            1295            1300                1305 att gac acc gcc tcc tac ggc ccc agc cat ggc agc acg gcc tcc       4390
Ile Asp Thr Ala Ser Tyr Gly Pro Ser His Gly Ser Thr Ala Ser
            1310            1315                1320 ctg ggg gcc tcc aca tcc tca cct cgt tca ggg cca ggc aaa gaa       4435
Leu Gly Ala Ser Thr Ser Ser Pro Arg Ser Gly Pro Gly Lys Glu
            1325            1330                1335 aag gtg gct ccc ctg tgg cac agc tcc agt gaa gtg ctc tcc ctg       4480
Lys Val Ala Pro Leu Trp His Ser Ser Ser Glu Val Leu Ser Leu
            1340            1345                1350 gca gat cgg acc tta gag act gag ggc cac ggc atg gac agg aaa       4525
Ala Asp Arg Thr Leu Glu Thr Glu Gly His Gly Met Asp Arg Lys
            1355            1360                1365 gca gag tcc tcc ctg agc ctg gac atc cac agc aag agc cag ggc       4570
Ala Glu Ser Ser Leu Ser Leu Asp Ile His Ser Lys Ser Gln Gly
            1370            1375                1380 ggg tca agc ccg ctg agc agg gag aac agc acc ttc agc ata aat       4615
Gly Ser Ser Pro Leu Ser Arg Glu Asn Ser Thr Phe Ser Ile Asn
            1385            1390                1395 gat gct gcg tcc cac acc agt acc atg agc tcc cga cac tct gcc       4660
Asp Ala Ala Ser His Thr Ser Thr Met Ser Ser Arg His Ser Ala
            1400            1405                1410 agc cca gtg gta ttc tcc agt gcc aga agt tcc ccc aaa gag gag       4705
Ser Pro Val Val Phe Ser Ser Ala Arg Ser Ser Pro Lys Glu Glu
            1415            1420                1425
```

```
ctt cac ccc acc gca tcc tcc cag ctc gca ccg tcc ttt tcc tct      4750
Leu His Pro Thr Ala Ser Ser Gln Leu Ala Pro Ser Phe Ser Ser
            1430                1435                1440 tct tcc tca tcc tcc tct gga cct agg act ttc tac cct cgc cag      4795
Ser Ser Ser Ser Ser Ser Gly Pro Arg Thr Phe Tyr Pro Arg Gln
            1445                1450                1455 ggc gcc act agc aaa tat ctg att gga tgg aaa aag cca gaa gga      4840
Gly Ala Thr Ser Lys Tyr Leu Ile Gly Trp Lys Lys Pro Glu Gly
            1460                1465                1470 acc att aac tcc gtg gga ttt atg gac aca cga aag cga cat cag      4885
Thr Ile Asn Ser Val Gly Phe Met Asp Thr Arg Lys Arg His Gln
            1475                1480                1485 agt gat ggc aat gag ata gcc cac act agg ctt cga gcc tca acc      4930
Ser Asp Gly Asn Glu Ile Ala His Thr Arg Leu Arg Ala Ser Thr
            1490                1495                1500 agg gac ctg cag gca tcc cca aag ccg acc tcc aag tct acc att      4975
Arg Asp Leu Gln Ala Ser Pro Lys Pro Thr Ser Lys Ser Thr Ile
            1505                1510                1515 gag gaa gat cta aag aaa ctc atc gac ctt gag agc cca act ccc      5020
Glu Glu Asp Leu Lys Lys Leu Ile Asp Leu Glu Ser Pro Thr Pro
            1520                1525                1530 gaa tcc cag aag aat ttc aag ttc cat gca ctg tcc tcc ccg cag      5065
Glu Ser Gln Lys Asn Phe Lys Phe His Ala Leu Ser Ser Pro Gln
            1535                1540                1545 tcc ccg ttc ccc act acc cct acc tcc cgg cgg gcc ctg cac agg      5110
Ser Pro Phe Pro Thr Thr Pro Thr Ser Arg Arg Ala Leu His Arg
            1550                1555                1560 act ctg tca gat gag agc att tac agc agc cag agg gag cat ttc      5155
Thr Leu Ser Asp Glu Ser Ile Tyr Ser Ser Gln Arg Glu His Phe
            1565                1570                1575 ttc acc tcc agg gct tcg ctt cta gac caa gcc ctg ccc aac gat      5200
Phe Thr Ser Arg Ala Ser Leu Leu Asp Gln Ala Leu Pro Asn Asp
            1580                1585                1590 gtc ctc ttc agc agt acc tac cca tct ctc ccc aag tca ctt cca      5245
Val Leu Phe Ser Ser Thr Tyr Pro Ser Leu Pro Lys Ser Leu Pro
            1595                1600                1605 ctg agg agg cca tct tac acg ttg gga atg aag tca ttg cat gga      5290
Leu Arg Arg Pro Ser Tyr Thr Leu Gly Met Lys Ser Leu His Gly
            1610                1615                1620 gag ttc tct gcc tcg gac agc tcc ctc acc gac atc cag gag acc      5335
Glu Phe Ser Ala Ser Asp Ser Ser Leu Thr Asp Ile Gln Glu Thr
            1625                1630                1635 cga agg cag cct atc cct gac cct ggc ctg atg ccc ctg cct gat      5380
Arg Arg Gln Pro Ile Pro Asp Pro Gly Leu Met Pro Leu Pro Asp
            1640                1645                1650 gca gct tca gat ttg gac tgg tcc aac cta gta gat gcc gcc aaa      5425
Ala Ala Ser Asp Leu Asp Trp Ser Asn Leu Val Asp Ala Ala Lys
            1655                1660                1665 gcc tat gag gtc cag aga gcc tca ttt ttt gct gct agt gat gaa      5470
Ala Tyr Glu Val Gln Arg Ala Ser Phe Phe Ala Ala Ser Asp Glu
            1670                1675                1680 aac cat cgc ccc ctg agc gcg gcc tcc aac agt gac cag ctg gag      5515
Asn His Arg Pro Leu Ser Ala Ala Ser Asn Ser Asp Gln Leu Glu
            1685                1690                1695 gag cag gcc ctg gtc cag atg aag tcc tac agc agt aag gac ccc      5560
Glu Gln Ala Leu Val Gln Met Lys Ser Tyr Ser Ser Lys Asp Pro
            1700                1705                1710 tct ccc act ctg gct tct aag gtg gac cag ctg gaa ggt atg ctg      5605
Ser Pro Thr Leu Ala Ser Lys Val Asp Gln Leu Glu Gly Met Leu
```

-continued

```
                    1715               1720               1725
aaa atg ctt cga  gaa gat ttg aag aag  gaa aaa gaa gac  aag gcc           5650
Lys Met Leu Arg  Glu Asp Leu Lys Lys  Glu Lys Glu Asp  Lys Ala
         1730                1735                 1740 cag ctg cag gcg  gaa gtt gag cac ctg  cgg gag gac aac  ctg agg           5695
Gln Leu Gln Ala  Glu Val Glu His Leu  Arg Glu Asp Asn  Leu Arg
         1745                1750                 1755 ctg cag gag gag  tcc cag aac gcc tcg  gac aag ctg aag  aag ttc           5740
Leu Gln Glu Glu  Ser Gln Asn Ala Ser  Asp Lys Leu Lys  Lys Phe
         1760                1765                 1770 aca gag tgg gtc  ttc aac acc ata gac  atg agc tag ggccagccga             5786
Thr Glu Trp Val  Phe Asn Thr Ile Asp  Met Ser
         1775                1780 ggggaaacga gaaagggaca ggctgcccta tgtgggcccc taaagcaccc attcacgcct        5846
tggaaagtat tctcagagtc cccagcgtcc cagcctgttc atatcggaca gtgcacagca        5906
caattgcaga tcaacaatca ttatctgcct tttttagaaa agaaaacaa aaaattaaat         5966 aaaaatttta aaagtaaaa taaaaattta actgctc                                  6003
```

<210> SEQ ID NO 2
<211> LENGTH: 1782
<212> TYPE: PRT
<213> ORGANISM: Mus musculus

<400> SEQUENCE: 2

```
Met Thr Ser Leu Lys Arg Ser Gln Thr Glu Arg Pro Val Thr Ala Asp
1               5                   10                  15

Arg Ala Ser Val Val Ser Thr Asp Gly Ala Pro Lys Val His Thr Asp
                20                  25                  30

Asp Phe Tyr Met Arg Arg Phe Arg Ser Gln Asn Gly Ser Leu Gly Ser
            35                  40                  45

Ser Val Met Ala Ala Val Gly Pro Pro Arg Ser Glu Gly Pro His His
        50                  55                  60

Ile Thr Ser Thr Pro Gly Val Pro Lys Met Gly Val Arg Ala Arg Ile
65                  70                  75                  80

Ala Asp Trp Pro Pro Arg Lys Glu Asn Val Lys Glu Ser Ser Arg Ser
                85                  90                  95

Ser Gln Glu Ile Glu Thr Ser Ser Cys Leu Glu Ser Leu Ser Ser Lys
            100                 105                 110

Gly Ser Pro Val Ser Gln Gly Ser Ser Val Ser Leu Asn Ser Asn Asp
        115                 120                 125

Ser Ala Met Leu Lys Ser Ile Gln Asn Thr Leu Lys Asn Lys Thr Gly
    130                 135                 140

Pro Ala Glu Ser Met Asp Ser Arg Phe Leu Met Pro Glu Ala Tyr Pro
145                 150                 155                 160

Ser Ser Pro Arg Lys Ala Leu Arg Arg Ile Arg Gln Arg Ser Asn Ser
                165                 170                 175

Asp Ile Thr Ile Ser Glu Leu Asp Val Asp Ser Phe Asp Glu Cys Ile
            180                 185                 190

Ser Pro Thr Tyr Lys Ser Gly Pro Ser Leu His Arg Glu Tyr Gly Ser
        195                 200                 205

Thr Ser Ser Ile Asp Lys Gln Gly Thr Ser Gly Asp Ser Phe Phe Asp
    210                 215                 220

Leu Leu Lys Gly Tyr Lys Asp Asp Arg Ser Asp Arg Gly Pro Thr Pro
225                 230                 235                 240
```

```
Thr Lys Leu Ser Asp Phe Leu Ile Thr Gly Gly Lys Gly Ser Gly
            245                 250                 255

Phe Ser Leu Asp Val Ile Asp Gly Pro Ile Ser Gln Arg Glu Asn Leu
        260                 265                 270

Arg Leu Phe Lys Glu Arg Glu Lys Pro Leu Lys Arg Arg Ser Lys Ser
        275                 280                 285

Glu Thr Gly Asp Ser Ser Ile Phe Arg Lys Leu Arg Asn Ala Lys Gly
    290                 295                 300

Glu Glu Leu Gly Lys Ser Ser Asp Leu Glu Asp Asn Arg Ser Glu Asp
305                 310                 315                 320

Ser Val Arg Pro Trp Thr Cys Pro Lys Cys Phe Ala His Tyr Asp Val
                325                 330                 335

Gln Ser Ile Leu Phe Asp Leu Asn Glu Ala Ile Met Asn Arg His Asn
            340                 345                 350

Val Ile Lys Arg Arg Asn Thr Thr Thr Gly Ala Ser Ala Ala Ala Val
        355                 360                 365

Ala Ser Leu Val Ser Gly Pro Leu Ser His Ser Ala Ser Phe Ser Ser
    370                 375                 380

Pro Met Gly Ser Thr Glu Asp Leu Asn Ser Lys Gly Ser Leu Gly Met
385                 390                 395                 400

Asp Gln Gly Asp Asp Lys Ser Asn Glu Leu Val Met Ser Cys Pro Tyr
                405                 410                 415

Phe Arg Asn Glu Ile Gly Gly Glu Gly Glu Arg Lys Ile Ser Leu Ser
            420                 425                 430

Lys Ser Asn Ser Gly Ser Phe Ser Gly Cys Glu Ser Thr Ser Phe Glu
        435                 440                 445

Ser Ala Leu Ser Ser His Cys Thr Asn Ala Gly Val Ala Val Leu Glu
    450                 455                 460

Val Pro Lys Glu Ser Leu Met Leu His Leu Asp Arg Val Lys Arg Tyr
465                 470                 475                 480

Thr Val Glu His Val Asp Leu Gly Ala Tyr Tyr Tyr Arg Lys Phe Phe
                485                 490                 495

Tyr Gln Lys Glu His Trp Asn Tyr Phe Gly Ala Asp Glu Asn Leu Gly
            500                 505                 510

Pro Val Ala Val Ser Ile Arg Arg Glu Lys Pro Glu Asp Met Lys Glu
        515                 520                 525

Asn Gly Ser Pro Tyr Asn Tyr Arg Ile Ile Phe Arg Thr Ser Glu Leu
    530                 535                 540

Met Thr Leu Arg Gly Ser Val Leu Glu Asp Ala Ile Pro Ser Thr Ala
545                 550                 555                 560

Lys His Ser Thr Ala Arg Gly Leu Pro Leu Lys Glu Val Leu Glu His
                565                 570                 575

Val Ile Pro Glu Leu Asn Val Gln Cys Leu Arg Leu Ala Phe Asn Thr
            580                 585                 590

Pro Lys Val Thr Glu Gln Leu Met Lys Leu Asp Glu Gln Gly Leu Asn
        595                 600                 605

Tyr Gln Gln Lys Val Gly Ile Met Tyr Cys Lys Ala Gly Gln Ser Thr
    610                 615                 620

Glu Glu Glu Met Tyr Asn Asn Glu Ser Ala Gly Pro Ala Phe Glu Glu
625                 630                 635                 640

Phe Leu Gln Leu Leu Gly Glu Arg Val Arg Leu Lys Gly Phe Glu Lys
                645                 650                 655

Tyr Arg Ala Gln Leu Asp Thr Lys Thr Asp Ser Thr Gly Thr His Ser
```

```
            660                 665                 670
Leu Tyr Thr Thr Tyr Lys Asp Tyr Glu Ile Met Phe His Val Ser Thr
                675                 680                 685
Met Leu Pro Tyr Thr Pro Asn Asn Lys Gln Gln Leu Leu Arg Lys Arg
        690                 695                 700
His Ile Gly Asn Asp Ile Val Thr Ile Val Phe Gln Glu Pro Gly Ala
705                 710                 715                 720
Gln Pro Phe Ser Pro Lys Asn Ile Arg Ser His Phe Gln His Val Phe
                725                 730                 735
Val Ile Val Arg Ala His Asn Pro Cys Thr Glu Ser Val Cys Tyr Ser
            740                 745                 750
Val Ala Val Thr Arg Ser Arg Asp Val Pro Ser Phe Gly Pro Pro Ile
            755                 760                 765
Pro Lys Gly Val Thr Phe Pro Lys Ser Asn Val Phe Arg Asp Phe Leu
        770                 775                 780
Leu Ala Lys Val Ile Asn Ala Glu Asn Ala Ala His Lys Ser Glu Lys
785                 790                 795                 800
Phe Arg Ala Met Ala Thr Arg Thr Arg Gln Glu Tyr Leu Lys Asp Leu
                805                 810                 815
Ala Glu Lys Asn Val Thr Asn Thr Pro Ile Asp Pro Ser Gly Lys Phe
            820                 825                 830
Pro Phe Ile Ser Leu Ala Ser Lys Lys Lys Lys Ser Lys Pro Tyr
            835                 840                 845
Pro Gly Ala Glu Leu Ser Asn Met Gly Ala Ile Val Trp Ala Val Arg
        850                 855                 860
Ala Lys Asp Tyr Asn Lys Ala Met Glu Phe Asp Cys Leu Leu Gly Ile
865                 870                 875                 880
Ser Ser Glu Phe Ile Val Leu Ile Glu Gln Thr Lys Ser Val Ala
                885                 890                 895
Phe Asn Cys Ser Cys Arg Asp Val Ile Gly Trp Thr Ser Ser Asp Thr
            900                 905                 910
Ser Leu Lys Ile Phe Tyr Glu Arg Gly Glu Cys Val Ser Val Glu Ser
            915                 920                 925
Phe Ile Ser Gly Glu Asp Ile Lys Glu Ile Val Arg Arg Leu Gln Phe
        930                 935                 940
Val Ser Lys Gly Cys Glu Ser Val Glu Met Thr Leu Arg Arg Asn Gly
945                 950                 955                 960
Leu Gly Gln Leu Gly Phe His Val Asn Tyr Glu Gly Ile Val Ala Asp
                965                 970                 975
Val Glu Pro Tyr Gly Tyr Ala Trp Gln Ala Gly Leu Arg Gln Gly Ser
            980                 985                 990
Arg Leu Val Glu Ile Cys Lys Val Ala Val Ala Thr Leu Ser His Glu
            995                1000                1005
Gln Met Ile Asp Leu Leu Arg Thr Ser Val Thr Val Lys Val Val
        1010                1015                1020
Ile Ile Pro Pro His Asp Asp Cys Thr Pro Arg Arg Ser Cys Ser
        1025                1030                1035
Glu Thr Tyr Arg Met Pro Val Met Glu Tyr Gln Met Asn Glu Gly
        1040                1045                1050
Ile Ser Tyr Glu Phe Lys Pro Phe Arg Asn Asn Asn Lys Trp
        1055                1060                1065
Gln Arg Asn Ala Ser Lys Gly Ala His Ser Pro Gln Val Pro Ser
        1070                1075                1080
```

```
Gln Leu Gln Ser Pro Met Thr Ser Arg Leu Asn Ala Gly Lys Gly
    1085            1090                1095

Asp Gly Lys Met Pro Pro Glu Arg Ala Ala Asn Ile Pro Arg
    1100            1105                1110

Ser Ile Ser Ser Asp Gly Arg Pro Leu Glu Arg Arg Leu Ser Pro
    1115            1120                1125

Gly Ser Asp Ile Tyr Val Thr Val Ser Ser Met Ala Leu Ala Arg
    1130            1135                1140

Ser Gln Cys Arg Asn Ser Pro Ser Asn Leu Ser Ser Ser Ser Glu
    1145            1150                1155

Thr Gly Ser Gly Gly Gly Thr Tyr Arg Gln Lys Ser Met Pro Glu
    1160            1165                1170

Gly Phe Gly Val Ser Arg Arg Ser Pro Ala Ser Ile Asp Arg Gln
    1175            1180                1185

Asn Thr Gln Ser Asp Ile Ser Gly Ser Gly Lys Ser Thr Pro Ser
    1190            1195                1200

Trp Gln Arg Ser Glu Asp Ser Leu Ala Asp Gln Met Glu Pro Thr
    1205            1210                1215

Cys His Leu Pro Ala Val Ser Lys Val Leu Pro Ala Phe Arg Glu
    1220            1225                1230

Ser Pro Ser Gly Arg Leu Met Arg Gln Asp Pro Val Val His Leu
    1235            1240                1245

Ser Pro Asn Lys Gln Gly His Ser Asp Ser His Tyr Ser Ser His
    1250            1255                1260

Ser Ser Ser Asn Thr Leu Ser Ser Asn Ala Ser Ser Ala His Ser
    1265            1270                1275

Asp Glu Lys Trp Tyr Asp Gly Asp Arg Thr Glu Ser Asp Leu Asn
    1280            1285                1290

Ser Tyr Asn Tyr Leu Gln Gly Thr Ser Ala Asp Ser Gly Ile Asp
    1295            1300                1305

Thr Ala Ser Tyr Gly Pro Ser His Gly Ser Thr Ala Ser Leu Gly
    1310            1315                1320

Ala Ser Thr Ser Ser Pro Arg Ser Gly Pro Gly Lys Glu Lys Val
    1325            1330                1335

Ala Pro Leu Trp His Ser Ser Ser Glu Val Leu Ser Leu Ala Asp
    1340            1345                1350

Arg Thr Leu Glu Thr Glu Gly His Gly Met Asp Arg Lys Ala Glu
    1355            1360                1365

Ser Ser Leu Ser Leu Asp Ile His Ser Lys Ser Gln Gly Gly Ser
    1370            1375                1380

Ser Pro Leu Ser Arg Glu Asn Ser Thr Phe Ser Ile Asn Asp Ala
    1385            1390                1395

Ala Ser His Thr Ser Thr Met Ser Ser Arg His Ser Ala Ser Pro
    1400            1405                1410

Val Val Phe Ser Ser Ala Arg Ser Ser Pro Lys Glu Glu Leu His
    1415            1420                1425

Pro Thr Ala Ser Ser Gln Leu Ala Pro Ser Phe Ser Ser Ser Ser
    1430            1435                1440

Ser Ser Ser Ser Gly Pro Arg Thr Phe Tyr Pro Arg Gln Gly Ala
    1445            1450                1455

Thr Ser Lys Tyr Leu Ile Gly Trp Lys Lys Pro Glu Gly Thr Ile
    1460            1465                1470
```

| | | | | | | | | | | | |
|---|---|---|---|---|---|---|---|---|---|---|---|
| Asn | Ser | Val | Gly | Phe | Met | Asp | Thr | Arg | Lys | Arg | His | Gln | Ser | Asp |
| 1475 | | | | 1480 | | | | | 1485 | | |

Asn Ser Val Gly Phe Met Asp Thr Arg Lys Arg His Gln Ser Asp
1475                1480                  1485

Gly Asn Glu Ile Ala His Thr Arg Leu Arg Ala Ser Thr Arg Asp
    1490                1495                  1500

Leu Gln Ala Ser Pro Lys Pro Thr Ser Lys Ser Thr Ile Glu Glu
1505                1510                  1515

Asp Leu Lys Lys Leu Ile Asp Leu Glu Ser Pro Thr Pro Glu Ser
1520                1525                  1530

Gln Lys Asn Phe Lys Phe His Ala Leu Ser Ser Pro Gln Ser Pro
1535                1540                  1545

Phe Pro Thr Thr Pro Thr Ser Arg Arg Ala Leu His Arg Thr Leu
1550                1555                  1560

Ser Asp Glu Ser Ile Tyr Ser Ser Gln Arg Glu His Phe Phe Thr
1565                1570                  1575

Ser Arg Ala Ser Leu Leu Asp Gln Ala Leu Pro Asn Asp Val Leu
1580                1585                  1590

Phe Ser Ser Thr Tyr Pro Ser Leu Pro Lys Ser Leu Pro Leu Arg
1595                1600                  1605

Arg Pro Ser Tyr Thr Leu Gly Met Lys Ser Leu His Gly Glu Phe
1610                1615                  1620

Ser Ala Ser Asp Ser Ser Leu Thr Asp Ile Gln Glu Thr Arg Arg
1625                1630                  1635

Gln Pro Ile Pro Asp Pro Gly Leu Met Pro Leu Pro Asp Ala Ala
1640                1645                  1650

Ser Asp Leu Asp Trp Ser Asn Leu Val Asp Ala Ala Lys Ala Tyr
1655                1660                  1665

Glu Val Gln Arg Ala Ser Phe Phe Ala Ala Ser Asp Glu Asn His
1670                1675                  1680

Arg Pro Leu Ser Ala Ala Ser Asn Ser Asp Gln Leu Glu Glu Gln
1685                1690                  1695

Ala Leu Val Gln Met Lys Ser Tyr Ser Ser Lys Asp Pro Ser Pro
1700                1705                  1710

Thr Leu Ala Ser Lys Val Asp Gln Leu Glu Gly Met Leu Lys Met
1715                1720                  1725

Leu Arg Glu Asp Leu Lys Lys Glu Lys Glu Asp Lys Ala Gln Leu
1730                1735                  1740

Gln Ala Glu Val Glu His Leu Arg Glu Asp Asn Leu Arg Leu Gln
1745                1750                  1755

Glu Glu Ser Gln Asn Ala Ser Asp Lys Leu Lys Lys Phe Thr Glu
1760                1765                  1770

Trp Val Phe Asn Thr Ile Asp Met Ser
1775                1780

<210> SEQ ID NO 3
<211> LENGTH: 6028
<212> TYPE: DNA
<213> ORGANISM: Homo sapiens
<220> FEATURE:
<221> NAME/KEY: CDS
<222> LOCATION: (349)..(5763)

<400> SEQUENCE: 3
ggtgtggacg ttgtctaaat ttcggtagcc atggcacaag aatataagaa agcatgggat    60
tatggcaacc acagaatctc agtagtacaa gttccattca gttttttctg aaagaaagcc   120
ctctgttaaa gtgaagcaaa gaaactgttg tggattataa cgtttagaag ttccaatttt   180

```
tcagtgcttt acaaataaag catcatttaa ccttttaaat gaaaaagatt aagatctcat         240
gcaactgttg tattttctgg aagccattct ccaaaaggga agtgcacatt taaaacacag         300
atatgatggt ccttgctgca gggatttaag tctacttgct tttacatc atg acc agc         357
                                                     Met Thr Ser
                                                      1 ttg aaa cgg tca cag aca gaa agg cct ctt gcc act gac agg gcc tct         405
Leu Lys Arg Ser Gln Thr Glu Arg Pro Leu Ala Thr Asp Arg Ala Ser
 5                  10                  15 gtt gtt ggc aca gac ggc acc ccc aaa gtc cac act gat gat ttc tac         453
Val Val Gly Thr Asp Gly Thr Pro Lys Val His Thr Asp Asp Phe Tyr
 20                  25                  30                  35 atg cgg cgc ttc cgg tcc caa aat ggc agc tta gga tca tca gtt atg         501
Met Arg Arg Phe Arg Ser Gln Asn Gly Ser Leu Gly Ser Ser Val Met
                 40                  45                  50 gct cct gta gga ccc ccc cga agt gaa ggt tct cac cat ata acc tca         549
Ala Pro Val Gly Pro Pro Arg Ser Glu Gly Ser His His Ile Thr Ser
             55                  60                  65 acc ccc gga gtc cca aaa atg ggg gta agg gca agg att gca gat tgg         597
Thr Pro Gly Val Pro Lys Met Gly Val Arg Ala Arg Ile Ala Asp Trp
         70                  75                  80 ccc cca aga aag gaa aac ata aaa gaa tct agc cgt tca agc cag gaa         645
Pro Pro Arg Lys Glu Asn Ile Lys Glu Ser Ser Arg Ser Ser Gln Glu
     85                  90                  95 ata gaa acc tca agt tgc ctt gat agc ctg tcc tcc aaa agc agt cct         693
Ile Glu Thr Ser Ser Cys Leu Asp Ser Leu Ser Ser Lys Ser Ser Pro
100                 105                 110                 115 gtg agt cag gga agt tct gtt agc ctc aat tcc aat gac tca gcc atg         741
Val Ser Gln Gly Ser Ser Val Ser Leu Asn Ser Asn Asp Ser Ala Met
                 120                 125                 130 ctg aaa agc ata cag aac acg ctg aaa aac aag aca aga ccg tcg gag         789
Leu Lys Ser Ile Gln Asn Thr Leu Lys Asn Lys Thr Arg Pro Ser Glu
             135                 140                 145 aac atg gac tcc aga ttt ctc atg cct gaa gcc tac ccc agc tcc ccc         837
Asn Met Asp Ser Arg Phe Leu Met Pro Glu Ala Tyr Pro Ser Ser Pro
         150                 155                 160 aga aaa gct ctt cgc aga ata cgc cag cga agc aac agt gat atc acc         885
Arg Lys Ala Leu Arg Arg Ile Arg Gln Arg Ser Asn Ser Asp Ile Thr
     165                 170                 175 ata agt gaa ctt gat gtg gat agc ttt gat gaa tgt atc tca cct aca         933
Ile Ser Glu Leu Asp Val Asp Ser Phe Asp Glu Cys Ile Ser Pro Thr
180                 185                 190                 195 tac aag act gga cca tca ctg cac agg gaa tat ggt agc aca tct tca         981
Tyr Lys Thr Gly Pro Ser Leu His Arg Glu Tyr Gly Ser Thr Ser Ser
                 200                 205                 210 att gat aaa cag gga aca tct gga gaa agc ttt ttt gat ttg tta aag        1029
Ile Asp Lys Gln Gly Thr Ser Gly Glu Ser Phe Phe Asp Leu Leu Lys
             215                 220                 225 ggc tac aaa gat gac aaa tct gat cga ggt cca act cca acc aag ctc        1077
Gly Tyr Lys Asp Asp Lys Ser Asp Arg Gly Pro Thr Pro Thr Lys Leu
         230                 235                 240 agt gac ttt ctc att act ggt ggt ggc aag ggt tct ggt ttc tct ttg        1125
Ser Asp Phe Leu Ile Thr Gly Gly Gly Lys Gly Ser Gly Phe Ser Leu
     245                 250                 255 gat gta ata gac ggg cct atc tca cag aga gag aac ctc agg ctt ttt        1173
Asp Val Ile Asp Gly Pro Ile Ser Gln Arg Glu Asn Leu Arg Leu Phe
260                 265                 270                 275 aag gaa agg gaa aaa cca ctc aag cga cgt tca aaa tct gaa act gga        1221
Lys Glu Arg Glu Lys Pro Leu Lys Arg Arg Ser Lys Ser Glu Thr Gly
```

-continued

|  |  |  | 280 |  |  |  | 285 |  |  |  | 290 |  |  |  |  |
|---|---|---|---|---|---|---|---|---|---|---|---|---|---|---|---|
| gac | tcc | tct | att | ttt | cgt | aaa | ttg | cgc | aat | gcc | aaa | ggt | gaa | gaa | ctt | 1269 |
| Asp | Ser | Ser | Ile | Phe | Arg | Lys | Leu | Arg | Asn | Ala | Lys | Gly | Glu | Glu | Leu |
|  |  |  | 295 |  |  |  | 300 |  |  |  | 305 |  |  |  |  |

| ggg | aag | tca | tca | gat | ctt | gaa | gat | aac | cga | tca | gaa | gac | tct | gtc | agg | 1317 |
| Gly | Lys | Ser | Ser | Asp | Leu | Glu | Asp | Asn | Arg | Ser | Glu | Asp | Ser | Val | Arg |
|  |  | 310 |  |  |  |  | 315 |  |  |  |  | 320 |  |  |  |

| ccc | tgg | aca | tgt | cca | aag | tgc | ttt | gcc | cac | tat | gat | gtc | cag | agt | ata | 1365 |
| Pro | Trp | Thr | Cys | Pro | Lys | Cys | Phe | Ala | His | Tyr | Asp | Val | Gln | Ser | Ile |
| 325 |  |  |  |  | 330 |  |  |  |  | 335 |  |  |  |  |  |

| tta | ttt | gat | ttg | aat | gag | gca | att | atg | aac | agg | cac | aat | gtt | att | aag | 1413 |
| Leu | Phe | Asp | Leu | Asn | Glu | Ala | Ile | Met | Asn | Arg | His | Asn | Val | Ile | Lys |
| 340 |  |  |  |  | 345 |  |  |  |  | 350 |  |  |  |  | 355 |

| agg | aga | aac | acc | acc | act | gga | gct | tcc | gca | gct | gcc | gtg | gca | tcc | ttg | 1461 |
| Arg | Arg | Asn | Thr | Thr | Thr | Gly | Ala | Ser | Ala | Ala | Ala | Val | Ala | Ser | Leu |
|  |  |  |  | 360 |  |  |  |  | 365 |  |  |  |  | 370 |  |

| gtc | tct | gga | cct | ctg | tct | cat | tca | gcc | agt | ttt | agc | tcc | cca | atg | ggc | 1509 |
| Val | Ser | Gly | Pro | Leu | Ser | His | Ser | Ala | Ser | Phe | Ser | Ser | Pro | Met | Gly |
|  |  |  | 375 |  |  |  |  | 380 |  |  |  |  | 385 |  |  |

| agc | aca | gag | gac | ctg | aat | tcc | aaa | gga | agc | ctc | agc | atg | gac | cag | gga | 1557 |
| Ser | Thr | Glu | Asp | Leu | Asn | Ser | Lys | Gly | Ser | Leu | Ser | Met | Asp | Gln | Gly |
|  |  | 390 |  |  |  |  | 395 |  |  |  |  | 400 |  |  |  |

| gat | gat | aaa | agc | aat | gag | ctt | gta | atg | agc | tgt | cca | tat | ttt | cgg | aat | 1605 |
| Asp | Asp | Lys | Ser | Asn | Glu | Leu | Val | Met | Ser | Cys | Pro | Tyr | Phe | Arg | Asn |
| 405 |  |  |  |  | 410 |  |  |  |  | 415 |  |  |  |  |  |

| gag | ata | ggt | gga | gaa | ggg | gag | agg | aaa | atc | agc | ctt | tca | aaa | tca | aat | 1653 |
| Glu | Ile | Gly | Gly | Glu | Gly | Glu | Arg | Lys | Ile | Ser | Leu | Ser | Lys | Ser | Asn |
| 420 |  |  |  |  | 425 |  |  |  |  | 430 |  |  |  |  | 435 |

| tct | ggc | tcc | ttt | agt | gga | tgt | gaa | agt | gcc | tcc | ttt | gag | tct | acc | ctt | 1701 |
| Ser | Gly | Ser | Phe | Ser | Gly | Cys | Glu | Ser | Ala | Ser | Phe | Glu | Ser | Thr | Leu |
|  |  |  |  | 440 |  |  |  |  | 445 |  |  |  |  | 450 |  |

| agt | tcc | cat | tgc | aca | aat | gca | gga | gtg | gca | gta | ctt | gaa | gtg | ccc | aag | 1749 |
| Ser | Ser | His | Cys | Thr | Asn | Ala | Gly | Val | Ala | Val | Leu | Glu | Val | Pro | Lys |
|  |  |  | 455 |  |  |  |  | 460 |  |  |  |  | 465 |  |  |

| gag | aac | ttg | gtg | ttg | cac | cta | gat | aga | gtg | aaa | aga | tac | atc | gtg | gaa | 1797 |
| Glu | Asn | Leu | Val | Leu | His | Leu | Asp | Arg | Val | Lys | Arg | Tyr | Ile | Val | Glu |
|  |  | 470 |  |  |  |  | 475 |  |  |  |  | 480 |  |  |  |

| cac | gta | gat | ctg | ggt | gca | tac | tat | tat | aga | aaa | ttt | ttc | tac | cag | aag | 1845 |
| His | Val | Asp | Leu | Gly | Ala | Tyr | Tyr | Tyr | Arg | Lys | Phe | Phe | Tyr | Gln | Lys |
| 485 |  |  |  |  | 490 |  |  |  |  | 495 |  |  |  |  |  |

| gaa | cac | tgg | aac | tat | ttt | ggg | gct | gat | gag | aat | ctt | ggt | cca | gtg | gct | 1893 |
| Glu | His | Trp | Asn | Tyr | Phe | Gly | Ala | Asp | Glu | Asn | Leu | Gly | Pro | Val | Ala |
| 500 |  |  |  |  | 505 |  |  |  |  | 510 |  |  |  |  | 515 |

| gtg | agc | att | cga | agg | gaa | aaa | cca | gat | gaa | atg | aaa | gaa | aat | gga | tct | 1941 |
| Val | Ser | Ile | Arg | Arg | Glu | Lys | Pro | Asp | Glu | Met | Lys | Glu | Asn | Gly | Ser |
|  |  |  |  | 520 |  |  |  |  | 525 |  |  |  |  | 530 |  |

| ccg | tac | aac | tac | cga | ata | att | ttt | aga | act | agt | gag | ctc | atg | aca | ctg | 1989 |
| Pro | Tyr | Asn | Tyr | Arg | Ile | Ile | Phe | Arg | Thr | Ser | Glu | Leu | Met | Thr | Leu |
|  |  |  | 535 |  |  |  |  | 540 |  |  |  |  | 545 |  |  |

| aga | ggt | tcg | gtc | ctg | gag | gac | gcc | att | ccg | tcg | aca | gcc | aag | cac | tcg | 2037 |
| Arg | Gly | Ser | Val | Leu | Glu | Asp | Ala | Ile | Pro | Ser | Thr | Ala | Lys | His | Ser |
|  |  | 550 |  |  |  |  | 555 |  |  |  |  | 560 |  |  |  |

| aca | gcc | aga | ggc | ctg | cct | ctc | aaa | gaa | gtg | ctc | gag | cac | gtg | gtt | cct | 2085 |
| Thr | Ala | Arg | Gly | Leu | Pro | Leu | Lys | Glu | Val | Leu | Glu | His | Val | Val | Pro |
| 565 |  |  |  |  | 570 |  |  |  |  | 575 |  |  |  |  |  |

| gag | ctc | aat | gtc | cag | tgc | ctg | cgg | ttg | gcc | ttc | aac | aca | ccc | aag | gtc | 2133 |
| Glu | Leu | Asn | Val | Gln | Cys | Leu | Arg | Leu | Ala | Phe | Asn | Thr | Pro | Lys | Val |
| 580 |  |  |  |  | 585 |  |  |  |  | 590 |  |  |  |  | 595 |

| aca | gag | cag | ctc | atg | aaa | ctg | gat | gaa | caa | ggg | ctg | aac | tac | cag | cag | 2181 |

```
Thr Glu Gln Leu Met Lys Leu Asp Glu Gln Gly Leu Asn Tyr Gln Gln
            600             605             610 aaa gta ggc atc atg tac tgc aaa gct gga cag agc act gaa gaa gag      2229
Lys Val Gly Ile Met Tyr Cys Lys Ala Gly Gln Ser Thr Glu Glu Glu
        615                 620                 625 atg tac aac aat gag tca gct ggc cca gcc ttt gaa gaa ttc ctt caa      2277
Met Tyr Asn Asn Glu Ser Ala Gly Pro Ala Phe Glu Glu Phe Leu Gln
            630                 635                 640 cta ttg gga gag cga gtt cgg ctc aaa gga ttt gag aag tat cga gca      2325
Leu Leu Gly Glu Arg Val Arg Leu Lys Gly Phe Glu Lys Tyr Arg Ala
        645                 650                 655 cag ctt gat acc aaa act gac tcc act gga acc cat tct ctg tac aca      2373
Gln Leu Asp Thr Lys Thr Asp Ser Thr Gly Thr His Ser Leu Tyr Thr
660                 665                 670                 675 aca tac aaa gat tat gaa att atg ttc cat gtt tct acc atg ctg cca      2421
Thr Tyr Lys Asp Tyr Glu Ile Met Phe His Val Ser Thr Met Leu Pro
                680                 685                 690 tac aca ccc aac aac aaa caa cag ctc ctg agg aag cgg cac att gga      2469
Tyr Thr Pro Asn Asn Lys Gln Gln Leu Leu Arg Lys Arg His Ile Gly
            695                 700                 705 aat gat atc gta aca att gtt ttc caa gag cct gga gca cag cca ttc      2517
Asn Asp Ile Val Thr Ile Val Phe Gln Glu Pro Gly Ala Gln Pro Phe
        710                 715                 720 agc cca aaa aac atc cga tcc cac ttc cag cac gtt ttc gtc atc gtc      2565
Ser Pro Lys Asn Ile Arg Ser His Phe Gln His Val Phe Val Ile Val
725                 730                 735 agg gtg cac aat ccg tgc tct gac agt gtc tgt tat agt gtg gct gtt      2613
Arg Val His Asn Pro Cys Ser Asp Ser Val Cys Tyr Ser Val Ala Val
740                 745                 750                 755 acc agg tcc aga gat gtg cct tcc ttt ggg cct ccc att cct aaa ggg      2661
Thr Arg Ser Arg Asp Val Pro Ser Phe Gly Pro Pro Ile Pro Lys Gly
                760                 765                 770 gtc act ttc cct aag tca aat gtg ttc agg gac ttc ctt ttg gcg aaa      2709
Val Thr Phe Pro Lys Ser Asn Val Phe Arg Asp Phe Leu Leu Ala Lys
            775                 780                 785 gtg att aat gca gaa aat gct gct cat aaa tcg gag aag ttt cgg gcc      2757
Val Ile Asn Ala Glu Asn Ala Ala His Lys Ser Glu Lys Phe Arg Ala
        790                 795                 800 atg gca act cgg acc cgc cag gaa tac ctg aaa gat ctg gca gaa aag      2805
Met Ala Thr Arg Thr Arg Gln Glu Tyr Leu Lys Asp Leu Ala Glu Lys
805                 810                 815 aat gtc acc aac acc cct atc gac cct tct ggc aag ttt ccg ttc atc      2853
Asn Val Thr Asn Thr Pro Ile Asp Pro Ser Gly Lys Phe Pro Phe Ile
820                 825                 830                 835 tct ctg gct tcc aag aag aag gaa aag tct aag cca tat cca gga gcc      2901
Ser Leu Ala Ser Lys Lys Lys Glu Lys Ser Lys Pro Tyr Pro Gly Ala
                840                 845                 850 gag ctc agc agc atg ggg gcc att gta tgg gca gtc cgg gct gaa gac      2949
Glu Leu Ser Ser Met Gly Ala Ile Val Trp Ala Val Arg Ala Glu Asp
            855                 860                 865 tac aac aag gcc atg gaa cta gac tgc ctt tta ggg atc tcc aat gag      2997
Tyr Asn Lys Ala Met Glu Leu Asp Cys Leu Leu Gly Ile Ser Asn Glu
        870                 875                 880 ttc att gtg ctc att gaa cag gaa aca aag agc gtg gtc ttc aat tgt      3045
Phe Ile Val Leu Ile Glu Gln Glu Thr Lys Ser Val Val Phe Asn Cys
885                 890                 895 tcc tgt aga gat gtg ata ggg tgg act tca act gac acc agc ctc aaa      3093
Ser Cys Arg Asp Val Ile Gly Trp Thr Ser Thr Asp Thr Ser Leu Lys
900                 905                 910                 915
```

-continued

| | |
|---|---|
| atc ttc tat gaa cga gga gaa tgt gtt tca gtg ggt agt ttt att aac<br>Ile Phe Tyr Glu Arg Gly Glu Cys Val Ser Val Gly Ser Phe Ile Asn<br>920                           925                     930 | 3141 |
| att gag gag atc aaa gag att gtc aaa agg ttg cag ttt gtt tca aaa<br>Ile Glu Glu Ile Lys Glu Ile Val Lys Arg Leu Gln Phe Val Ser Lys<br>935                         940                     945 | 3189 |
| ggc tgt gaa tcg gtg gag atg act ctg cga aga aat ggg cta gga cag<br>Gly Cys Glu Ser Val Glu Met Thr Leu Arg Arg Asn Gly Leu Gly Gln<br>950                         955                     960 | 3237 |
| ctt ggc ttc cat gtc aac tat gag ggc att gtg gcg gat gtg gag ccc<br>Leu Gly Phe His Val Asn Tyr Glu Gly Ile Val Ala Asp Val Glu Pro<br>965                         970                     975 | 3285 |
| tac ggt tat gcc tgg cag gca ggg ctg agg cag ggc agt cgc ctg gtg<br>Tyr Gly Tyr Ala Trp Gln Ala Gly Leu Arg Gln Gly Ser Arg Leu Val<br>980                         985                     990                     995 | 3333 |
| gag atc tgc aag gtg gcg gta gcc act ctg agc cat gag cag atg<br>Glu Ile Cys Lys Val Ala Val Ala Thr Leu Ser His Glu Gln Met<br>                         1000                    1005                  1010 | 3378 |
| atc gac ctc ctg aga aca tct gtc acg gtg aag gtt gtc atc att<br>Ile Asp Leu Leu Arg Thr Ser Val Thr Val Lys Val Val Ile Ile<br>                         1015                    1020                  1025 | 3423 |
| ccc ccg cat gat gac tgc acc ccg cgg agg agt tgc tct gaa acc<br>Pro Pro His Asp Asp Cys Thr Pro Arg Arg Ser Cys Ser Glu Thr<br>                         1030                    1035                  1040 | 3468 |
| tac cgc atg cca gtg atg gag tac aaa atg aat gaa ggt gtt tca<br>Tyr Arg Met Pro Val Met Glu Tyr Lys Met Asn Glu Gly Val Ser<br>                         1045                    1050                  1055 | 3513 |
| tac gaa ttc aag ttt ccc ttc cga aat aat aac aag tgg cag agg<br>Tyr Glu Phe Lys Phe Pro Phe Arg Asn Asn Asn Lys Trp Gln Arg<br>                         1060                    1065                  1070 | 3558 |
| aac gcc agc aag ggg cct cat tca cct caa gtc ccg tcc cag gtg<br>Asn Ala Ser Lys Gly Pro His Ser Pro Gln Val Pro Ser Gln Val<br>                         1075                    1080                  1085 | 3603 |
| cag agt ccc atg acc tcg cgg ctg aat gct gga aaa gga gat ggg<br>Gln Ser Pro Met Thr Ser Arg Leu Asn Ala Gly Lys Gly Asp Gly<br>                         1090                    1095                  1100 | 3648 |
| aag atg cct cct cca gaa aga gcc gcc aac atc cct cga agc atc<br>Lys Met Pro Pro Pro Glu Arg Ala Ala Asn Ile Pro Arg Ser Ile<br>                         1105                    1110                  1115 | 3693 |
| tcc agt gac ggg cgc cca cta gag agg cgg ctg tct cct ggt tcg<br>Ser Ser Asp Gly Arg Pro Leu Glu Arg Arg Leu Ser Pro Gly Ser<br>                         1120                    1125                  1130 | 3738 |
| gac atc tat gtg acg gtc tca tcc atg gct tta gca aga tcc cag<br>Asp Ile Tyr Val Thr Val Ser Ser Met Ala Leu Ala Arg Ser Gln<br>                         1135                    1140                  1145 | 3783 |
| tgt cgg aac tct cct agc aac ttg tct tca tcc agt gat act ggt<br>Cys Arg Asn Ser Pro Ser Asn Leu Ser Ser Ser Ser Asp Thr Gly<br>                         1150                    1155                  1160 | 3828 |
| tct gtg ggg ggc act tac agg cag aag tcc atg ccc gaa ggg ttt<br>Ser Val Gly Gly Thr Tyr Arg Gln Lys Ser Met Pro Glu Gly Phe<br>                         1165                    1170                  1175 | 3873 |
| gga gtg agc cgt aga tcc cca gcc tcc att gac agg cag aac acc<br>Gly Val Ser Arg Arg Ser Pro Ala Ser Ile Asp Arg Gln Asn Thr<br>                         1180                    1185                  1190 | 3918 |
| cag tca gat att ggt ggc agc gga aaa tcc acg cct agc tgg caa<br>Gln Ser Asp Ile Gly Gly Ser Gly Lys Ser Thr Pro Ser Trp Gln<br>                         1195                    1200                  1205 | 3963 |
| aga agt gag gat agc att gct gac cag atg gct tac agt tat aga<br>Arg Ser Glu Asp Ser Ile Ala Asp Gln Met Ala Tyr Ser Tyr Arg<br>                         1210                    1215                  1220 | 4008 |

```
gga cct cag gat ttc  aat tct ttt gtc ctc  gag cag cat gaa tat      4053
Gly Pro Gln Asp Phe  Asn Ser Phe Val Leu  Glu Gln His Glu Tyr
                1225                 1230                 1235 aca gag cca aca tgc  cat ctc cca gca gta  tca aag gta ctg cca      4098
Thr Glu Pro Thr Cys  His Leu Pro Ala Val  Ser Lys Val Leu Pro
                1240                 1245                 1250 gct ttc cga gag agc  ccc agt ggg aga tta  atg cgg cag gat cca      4143
Ala Phe Arg Glu Ser  Pro Ser Gly Arg Leu  Met Arg Gln Asp Pro
                1255                 1260                 1265 gtg gtt cat ttg tct  cca aac aaa caa ggg  cat tct gat agc cac      4188
Val Val His Leu Ser  Pro Asn Lys Gln Gly  His Ser Asp Ser His
                1270                 1275                 1280 tac tcg agc cac tcc  agt agc aat act ctc  tcc agc aat gcg tca      4233
Tyr Ser Ser His Ser  Ser Ser Asn Thr Leu  Ser Ser Asn Ala Ser
                1285                 1290                 1295 agt gcc cat agt gat  gag aag tgg tac gat  ggg gac cgc aca gaa      4278
Ser Ala His Ser Asp  Glu Lys Trp Tyr Asp  Gly Asp Arg Thr Glu
                1300                 1305                 1310 tcc gaa ctc aac agc  tat aac tat ctg caa  ggc acc tct gct gac      4323
Ser Glu Leu Asn Ser  Tyr Asn Tyr Leu Gln  Gly Thr Ser Ala Asp
                1315                 1320                 1325 agt ggc att gac acc  acc tct tat ggc ccc  agc cac ggc agc aca      4368
Ser Gly Ile Asp Thr  Thr Ser Tyr Gly Pro  Ser His Gly Ser Thr
                1330                 1335                 1340 gcc tcg ctg ggg gct  gcc aca tcg tca cct  cgc tca ggg cca ggc      4413
Ala Ser Leu Gly Ala  Ala Thr Ser Ser Pro  Arg Ser Gly Pro Gly
                1345                 1350                 1355 aag gag aaa gtg gca  ccc cta tgg cac agc  tcc agt gaa gta atc      4458
Lys Glu Lys Val Ala  Pro Leu Trp His Ser  Ser Ser Glu Val Ile
                1360                 1365                 1370 tcc atg gca gat cgg  act ttg gag aca gag  agc cac ggc ctg gac      4503
Ser Met Ala Asp Arg  Thr Leu Glu Thr Glu  Ser His Gly Leu Asp
                1375                 1380                 1385 cgg aaa aca gag tct  tcc ctg agc tta gac  ata cac agc aag agc      4548
Arg Lys Thr Glu Ser  Ser Leu Ser Leu Asp  Ile His Ser Lys Ser
                1390                 1395                 1400 caa gcc ggc tcg acc  cct ctg aca agg gag  aac agc acc ttc agt      4593
Gln Ala Gly Ser Thr  Pro Leu Thr Arg Glu  Asn Ser Thr Phe Ser
                1405                 1410                 1415 ata aac gat gct gct  tcc cac aca agt acc  atg agc tcc cga cac      4638
Ile Asn Asp Ala Ala  Ser His Thr Ser Thr  Met Ser Ser Arg His
                1420                 1425                 1430 tct gcc agc cca gtg  gtt ttc acc agt gcc  cgg agt tca cct aaa      4683
Ser Ala Ser Pro Val  Val Phe Thr Ser Ala  Arg Ser Ser Pro Lys
                1435                 1440                 1445 gaa gag ctt cat cca  gct gcc ccc tca cag  ctc gca cca tcc ttc      4728
Glu Glu Leu His Pro  Ala Ala Pro Ser Gln  Leu Ala Pro Ser Phe
                1450                 1455                 1460 tcc tcc tct tcc tcc  tcc tcc tct ggt cct  agg agt ttt tac cct      4773
Ser Ser Ser Ser Ser  Ser Ser Ser Gly Pro  Arg Ser Phe Tyr Pro
                1465                 1470                 1475 cgc cag ggc gct act  agc aag tac ctg att  gga tgg aaa aaa ccc      4818
Arg Gln Gly Ala Thr  Ser Lys Tyr Leu Ile  Gly Trp Lys Lys Pro
                1480                 1485                 1490 gaa gga acc ata aac  tcc gtg gga ttt atg  gac acg aga aag cgt      4863
Glu Gly Thr Ile Asn  Ser Val Gly Phe Met  Asp Thr Arg Lys Arg
                1495                 1500                 1505 cat cag agc gat ggc  aat gaa ata gcc cac  acc agg ctg cgt gcc      4908
His Gln Ser Asp Gly  Asn Glu Ile Ala His  Thr Arg Leu Arg Ala
```

```
                              1510                  1515                 1520 tca  acc  aga  gac  ctc  cgg  gca  tct  cct  aag  cca  acc  tcc  aag  tcc      4953
Ser  Thr  Arg  Asp  Leu  Arg  Ala  Ser  Pro  Lys  Pro  Thr  Ser  Lys  Ser
               1525                      1530                     1535 acc  att  gaa  gaa  gat  cta  aag  aaa  cta  att  gat  ctt  gaa  agc  cca      4998
Thr  Ile  Glu  Glu  Asp  Leu  Lys  Lys  Leu  Ile  Asp  Leu  Glu  Ser  Pro
               1540                      1545                     1550 act  cct  gaa  tca  cag  aag  agt  ttt  aag  ttc  cac  gca  ctc  tcc  tct      5043
Thr  Pro  Glu  Ser  Gln  Lys  Ser  Phe  Lys  Phe  His  Ala  Leu  Ser  Ser
               1555                      1560                     1565 cct  cag  tct  cct  ttc  ccc  agc  acc  ccc  acc  tca  cgg  cgg  gcc  ttg      5088
Pro  Gln  Ser  Pro  Phe  Pro  Ser  Thr  Pro  Thr  Ser  Arg  Arg  Ala  Leu
               1570                      1575                     1580 cac  aga  aca  ctg  tcg  gac  gag  agc  att  tac  aat  agc  cag  agg  gag      5133
His  Arg  Thr  Leu  Ser  Asp  Glu  Ser  Ile  Tyr  Asn  Ser  Gln  Arg  Glu
               1585                      1590                     1595 cac  ttt  ttc  acc  tcc  agg  gcg  tca  ctt  ctg  gac  caa  gcc  ctg  ccc      5178
His  Phe  Phe  Thr  Ser  Arg  Ala  Ser  Leu  Leu  Asp  Gln  Ala  Leu  Pro
               1600                      1605                     1610 aac  gac  gtc  ctc  ttc  agt  agc  acg  tac  cct  tct  ctc  ccc  aag  tcg      5223
Asn  Asp  Val  Leu  Phe  Ser  Ser  Thr  Tyr  Pro  Ser  Leu  Pro  Lys  Ser
               1615                      1620                     1625 ctc  ccg  ttg  agg  agg  cct  tct  tac  acc  tta  gga  atg  aaa  tcg  ctg      5268
Leu  Pro  Leu  Arg  Arg  Pro  Ser  Tyr  Thr  Leu  Gly  Met  Lys  Ser  Leu
               1630                      1635                     1640 cat  gga  gag  ttc  tca  gcc  tcg  gac  agc  tcc  ctc  act  gac  atc  cag      5313
His  Gly  Glu  Phe  Ser  Ala  Ser  Asp  Ser  Ser  Leu  Thr  Asp  Ile  Gln
               1645                      1650                     1655 gag  acc  cgc  agg  cag  cct  atg  ccc  gac  cct  ggc  ctg  atg  ccc  ctg      5358
Glu  Thr  Arg  Arg  Gln  Pro  Met  Pro  Asp  Pro  Gly  Leu  Met  Pro  Leu
               1660                      1665                     1670 cct  gac  act  gct  gca  gac  ttg  gat  tgg  tcc  aac  ctg  gta  gat  gct      5403
Pro  Asp  Thr  Ala  Ala  Asp  Leu  Asp  Trp  Ser  Asn  Leu  Val  Asp  Ala
               1675                      1680                     1685 gcc  aaa  gcc  tat  gag  gtc  cag  aga  gcc  tca  ttt  ttt  gct  gct  agt      5448
Ala  Lys  Ala  Tyr  Glu  Val  Gln  Arg  Ala  Ser  Phe  Phe  Ala  Ala  Ser
               1690                      1695                     1700 gat  gaa  aac  cat  cgc  ccc  ttg  agt  gct  gca  tcc  aac  agt  gat  cag      5493
Asp  Glu  Asn  His  Arg  Pro  Leu  Ser  Ala  Ala  Ser  Asn  Ser  Asp  Gln
               1705                      1710                     1715 ctg  gag  gac  cag  gct  ctg  gcc  cag  atg  aag  cct  tac  agc  agc  agt      5538
Leu  Glu  Asp  Gln  Ala  Leu  Ala  Gln  Met  Lys  Pro  Tyr  Ser  Ser  Ser
               1720                      1725                     1730 aaa  gac  tcc  tct  ccc  act  ctg  gct  tct  aaa  gtg  gac  cag  ctg  gaa      5583
Lys  Asp  Ser  Ser  Pro  Thr  Leu  Ala  Ser  Lys  Val  Asp  Gln  Leu  Glu
               1735                      1740                     1745 ggt  atg  ctg  aag  atg  ctt  cgg  gaa  gat  ttg  aag  aag  gaa  aaa  gaa      5628
Gly  Met  Leu  Lys  Met  Leu  Arg  Glu  Asp  Leu  Lys  Lys  Glu  Lys  Glu
               1750                      1755                     1760 gac  aaa  gct  cac  ctt  cag  gcg  gag  gtg  cag  cac  ctg  cga  gag  gac      5673
Asp  Lys  Ala  His  Leu  Gln  Ala  Glu  Val  Gln  His  Leu  Arg  Glu  Asp
               1765                      1770                     1775 aac  ctg  agg  cta  cag  gag  gag  tcc  cag  aac  gcc  tcg  gac  aag  ctg      5718
Asn  Leu  Arg  Leu  Gln  Glu  Glu  Ser  Gln  Asn  Ala  Ser  Asp  Lys  Leu
               1780                      1785                     1790 aag  aag  ttc  aca  gaa  tgg  gtc  ttc  aac  acc  ata  gac  atg  agc  tag      5763
Lys  Lys  Phe  Thr  Glu  Trp  Val  Phe  Asn  Thr  Ile  Asp  Met  Ser
               1795                      1800 ggaaggctga  ggaggacagg  agaagggccc  agacactccc  tccagtgagt  gtcctgcagc         5823
```

```
cattattccc tccatagaaa gcatcctcag agcaccttcc ctggcttcct actctgcccc    5883
ctttcgggga gtgcacaaca caatagttgc agatcaacaa tcatcacctg cctttttgtag   5943 aaaagaaaaa caaaaaaagt aaataaaaat tttaaacagt aaaataaaag tttaactgct    6003
aaaaaaaaaa aaaaaaaaaa aaaaa                                          6028
```

<210> SEQ ID NO 4
<211> LENGTH: 1804
<212> TYPE: PRT
<213> ORGANISM: Homo sapiens

<400> SEQUENCE: 4

```
Met Thr Ser Leu Lys Arg Ser Gln Thr Glu Arg Pro Leu Ala Thr Asp
1               5                   10                  15

Arg Ala Ser Val Val Gly Thr Asp Gly Thr Pro Lys Val His Thr Asp
            20                  25                  30

Asp Phe Tyr Met Arg Arg Phe Arg Ser Gln Asn Gly Ser Leu Gly Ser
        35                  40                  45

Ser Val Met Ala Pro Val Gly Pro Pro Arg Ser Glu Gly Ser His His
    50                  55                  60

Ile Thr Ser Thr Pro Gly Val Pro Lys Met Gly Val Arg Ala Arg Ile
65                  70                  75                  80

Ala Asp Trp Pro Pro Arg Lys Glu Asn Ile Lys Glu Ser Ser Arg Ser
                85                  90                  95

Ser Gln Glu Ile Glu Thr Ser Ser Cys Leu Asp Ser Leu Ser Ser Lys
            100                 105                 110

Ser Ser Pro Val Ser Gln Gly Ser Ser Val Ser Leu Asn Ser Asn Asp
        115                 120                 125

Ser Ala Met Leu Lys Ser Ile Gln Asn Thr Leu Lys Asn Lys Thr Arg
    130                 135                 140

Pro Ser Glu Asn Met Asp Ser Arg Phe Leu Met Pro Glu Ala Tyr Pro
145                 150                 155                 160

Ser Ser Pro Arg Lys Ala Leu Arg Arg Ile Arg Gln Arg Ser Asn Ser
                165                 170                 175

Asp Ile Thr Ile Ser Glu Leu Asp Val Asp Ser Phe Asp Glu Cys Ile
            180                 185                 190

Ser Pro Thr Tyr Lys Thr Gly Pro Ser Leu His Arg Glu Tyr Gly Ser
        195                 200                 205

Thr Ser Ser Ile Asp Lys Gln Gly Thr Ser Gly Glu Ser Phe Phe Asp
    210                 215                 220

Leu Leu Lys Gly Tyr Lys Asp Asp Lys Ser Asp Arg Gly Pro Thr Pro
225                 230                 235                 240

Thr Lys Leu Ser Asp Phe Leu Ile Thr Gly Gly Gly Lys Gly Ser Gly
                245                 250                 255

Phe Ser Leu Asp Val Ile Asp Gly Pro Ile Ser Gln Arg Glu Asn Leu
            260                 265                 270

Arg Leu Phe Lys Glu Arg Glu Lys Pro Leu Lys Arg Arg Ser Lys Ser
        275                 280                 285

Glu Thr Gly Asp Ser Ser Ile Phe Arg Lys Leu Arg Asn Ala Lys Gly
    290                 295                 300

Glu Glu Leu Gly Lys Ser Ser Asp Leu Glu Asp Asn Arg Ser Glu Asp
305                 310                 315                 320

Ser Val Arg Pro Trp Thr Cys Pro Lys Cys Phe Ala His Tyr Asp Val
                325                 330                 335
```

```
Gln Ser Ile Leu Phe Asp Leu Asn Glu Ala Ile Met Asn Arg His Asn
            340                 345                 350

Val Ile Lys Arg Arg Asn Thr Thr Gly Ala Ser Ala Ala Val
            355                 360                 365

Ala Ser Leu Val Ser Gly Pro Leu Ser His Ser Ala Ser Phe Ser Ser
370                 375                 380

Pro Met Gly Ser Thr Glu Asp Leu Asn Ser Lys Gly Ser Leu Ser Met
385                 390                 395                 400

Asp Gln Gly Asp Asp Lys Ser Asn Glu Leu Val Met Ser Cys Pro Tyr
                405                 410                 415

Phe Arg Asn Glu Ile Gly Gly Glu Arg Lys Ile Ser Leu Ser
            420                 425                 430

Lys Ser Asn Ser Gly Ser Phe Ser Gly Cys Glu Ser Ala Ser Phe Glu
            435                 440                 445

Ser Thr Leu Ser Ser His Cys Thr Asn Ala Gly Val Ala Val Leu Glu
            450                 455                 460

Val Pro Lys Glu Asn Leu Val Leu His Leu Asp Arg Val Lys Arg Tyr
465                 470                 475                 480

Ile Val Glu His Val Asp Leu Gly Ala Tyr Tyr Tyr Arg Lys Phe Phe
                485                 490                 495

Tyr Gln Lys Glu His Trp Asn Tyr Phe Gly Ala Asp Glu Asn Leu Gly
            500                 505                 510

Pro Val Ala Val Ser Ile Arg Arg Glu Lys Pro Asp Glu Met Lys Glu
            515                 520                 525

Asn Gly Ser Pro Tyr Asn Tyr Arg Ile Ile Phe Arg Thr Ser Glu Leu
            530                 535                 540

Met Thr Leu Arg Gly Ser Val Leu Glu Asp Ala Ile Pro Ser Thr Ala
545                 550                 555                 560

Lys His Ser Thr Ala Arg Gly Leu Pro Leu Lys Glu Val Leu Glu His
                565                 570                 575

Val Val Pro Glu Leu Asn Val Gln Cys Leu Arg Leu Ala Phe Asn Thr
            580                 585                 590

Pro Lys Val Thr Glu Gln Leu Met Lys Leu Asp Glu Gln Gly Leu Asn
            595                 600                 605

Tyr Gln Gln Lys Val Gly Ile Met Tyr Cys Lys Ala Gly Gln Ser Thr
610                 615                 620

Glu Glu Glu Met Tyr Asn Asn Glu Ser Ala Gly Pro Ala Phe Glu Glu
625                 630                 635                 640

Phe Leu Gln Leu Leu Gly Glu Arg Val Arg Leu Lys Gly Phe Glu Lys
                645                 650                 655

Tyr Arg Ala Gln Leu Asp Thr Lys Thr Asp Ser Thr Gly Thr His Ser
            660                 665                 670

Leu Tyr Thr Thr Tyr Lys Asp Tyr Glu Ile Met Phe His Val Ser Thr
            675                 680                 685

Met Leu Pro Tyr Thr Pro Asn Asn Lys Gln Gln Leu Leu Arg Lys Arg
            690                 695                 700

His Ile Gly Asn Asp Ile Val Thr Ile Val Phe Gln Glu Pro Gly Ala
705                 710                 715                 720

Gln Pro Phe Ser Pro Lys Asn Ile Arg Ser His Phe Gln His Val Phe
                725                 730                 735

Val Ile Val Arg Val His Asn Pro Cys Ser Asp Ser Val Cys Tyr Ser
            740                 745                 750
```

Val Ala Val Thr Arg Ser Arg Asp Val Pro Ser Phe Gly Pro Pro Ile
            755                 760                 765

Pro Lys Gly Val Thr Phe Pro Lys Ser Asn Val Phe Arg Asp Phe Leu
    770                 775                 780

Leu Ala Lys Val Ile Asn Ala Glu Asn Ala Ala His Lys Ser Glu Lys
785                 790                 795                 800

Phe Arg Ala Met Ala Thr Arg Thr Arg Gln Glu Tyr Leu Lys Asp Leu
                805                 810                 815

Ala Glu Lys Asn Val Thr Asn Thr Pro Ile Asp Pro Ser Gly Lys Phe
            820                 825                 830

Pro Phe Ile Ser Leu Ala Ser Lys Lys Lys Lys Ser Lys Pro Tyr
        835                 840                 845

Pro Gly Ala Glu Leu Ser Ser Met Gly Ala Ile Val Trp Ala Val Arg
    850                 855                 860

Ala Glu Asp Tyr Asn Lys Ala Met Glu Leu Asp Cys Leu Leu Gly Ile
865                 870                 875                 880

Ser Asn Glu Phe Ile Val Leu Ile Glu Gln Thr Lys Ser Val Val
                885                 890                 895

Phe Asn Cys Ser Cys Arg Asp Val Ile Gly Trp Thr Ser Thr Asp Thr
            900                 905                 910

Ser Leu Lys Ile Phe Tyr Glu Arg Gly Glu Cys Val Ser Val Gly Ser
    915                 920                 925

Phe Ile Asn Ile Glu Glu Ile Lys Glu Ile Val Lys Arg Leu Gln Phe
930                 935                 940

Val Ser Lys Gly Cys Glu Ser Val Glu Met Thr Leu Arg Arg Asn Gly
945                 950                 955                 960

Leu Gly Gln Leu Gly Phe His Val Asn Tyr Glu Gly Ile Val Ala Asp
                965                 970                 975

Val Glu Pro Tyr Gly Tyr Ala Trp Gln Ala Gly Leu Arg Gln Gly Ser
            980                 985                 990

Arg Leu Val Glu Ile Cys Lys Val Ala Val Ala Thr Leu Ser His Glu
    995                 1000                1005

Gln Met Ile Asp Leu Leu Arg Thr Ser Val Thr Val Lys Val Val
    1010                1015                1020

Ile Ile Pro Pro His Asp Asp Cys Thr Pro Arg Ser Cys Ser
    1025                1030                1035

Glu Thr Tyr Arg Met Pro Val Met Glu Tyr Lys Met Asn Glu Gly
    1040                1045                1050

Val Ser Tyr Glu Phe Lys Phe Pro Phe Arg Asn Asn Lys Trp
    1055                1060                1065

Gln Arg Asn Ala Ser Lys Gly Pro His Ser Pro Gln Val Pro Ser
    1070                1075                1080

Gln Val Gln Ser Pro Met Thr Ser Arg Leu Asn Ala Gly Lys Gly
    1085                1090                1095

Asp Gly Lys Met Pro Pro Glu Arg Ala Ala Asn Ile Pro Arg
    1100                1105                1110

Ser Ile Ser Ser Asp Gly Arg Pro Leu Glu Arg Arg Leu Ser Pro
    1115                1120                1125

Gly Ser Asp Ile Tyr Val Thr Val Ser Ser Met Ala Leu Ala Arg
    1130                1135                1140

Ser Gln Cys Arg Asn Ser Pro Ser Asn Leu Ser Ser Ser Ser Asp
    1145                1150                1155

Thr Gly Ser Val Gly Gly Thr Tyr Arg Gln Lys Ser Met Pro Glu

```
            1160                1165                1170
Gly Phe Gly Val Ser Arg Arg Ser Pro Ala Ser Ile Asp Arg Gln
    1175                1180                1185
Asn Thr Gln Ser Asp Ile Gly Gly Ser Gly Lys Ser Thr Pro Ser
    1190                1195                1200
Trp Gln Arg Ser Glu Asp Ser Ile Ala Asp Gln Met Ala Tyr Ser
    1205                1210                1215
Tyr Arg Gly Pro Gln Asp Phe Asn Ser Phe Val Leu Glu Gln His
    1220                1225                1230
Glu Tyr Thr Glu Pro Thr Cys His Leu Pro Ala Val Ser Lys Val
    1235                1240                1245
Leu Pro Ala Phe Arg Glu Ser Pro Ser Gly Arg Leu Met Arg Gln
    1250                1255                1260
Asp Pro Val Val His Leu Ser Pro Asn Lys Gln Gly His Ser Asp
    1265                1270                1275
Ser His Tyr Ser Ser His Ser Ser Ser Asn Thr Leu Ser Ser Asn
    1280                1285                1290
Ala Ser Ser Ala His Ser Asp Glu Lys Trp Tyr Asp Gly Asp Arg
    1295                1300                1305
Thr Glu Ser Glu Leu Asn Ser Tyr Asn Tyr Leu Gln Gly Thr Ser
    1310                1315                1320
Ala Asp Ser Gly Ile Asp Thr Thr Ser Tyr Gly Pro Ser His Gly
    1325                1330                1335
Ser Thr Ala Ser Leu Gly Ala Ala Thr Ser Ser Pro Arg Ser Gly
    1340                1345                1350
Pro Gly Lys Glu Lys Val Ala Pro Leu Trp His Ser Ser Ser Glu
    1355                1360                1365
Val Ile Ser Met Ala Asp Arg Thr Leu Glu Thr Glu Ser His Gly
    1370                1375                1380
Leu Asp Arg Lys Thr Glu Ser Ser Leu Ser Leu Asp Ile His Ser
    1385                1390                1395
Lys Ser Gln Ala Gly Ser Thr Pro Leu Thr Arg Glu Asn Ser Thr
    1400                1405                1410
Phe Ser Ile Asn Asp Ala Ala Ser His Thr Ser Thr Met Ser Ser
    1415                1420                1425
Arg His Ser Ala Ser Pro Val Val Phe Thr Ser Ala Arg Ser Ser
    1430                1435                1440
Pro Lys Glu Glu Leu His Pro Ala Ala Pro Ser Gln Leu Ala Pro
    1445                1450                1455
Ser Phe Ser Ser Ser Ser Ser Ser Ser Gly Pro Arg Ser Phe
    1460                1465                1470
Tyr Pro Arg Gln Gly Ala Thr Ser Lys Tyr Leu Ile Gly Trp Lys
    1475                1480                1485
Lys Pro Glu Gly Thr Ile Asn Ser Val Gly Phe Met Asp Thr Arg
    1490                1495                1500
Lys Arg His Gln Ser Asp Gly Asn Glu Ile Ala His Thr Arg Leu
    1505                1510                1515
Arg Ala Ser Thr Arg Asp Leu Arg Ala Ser Pro Lys Pro Thr Ser
    1520                1525                1530
Lys Ser Thr Ile Glu Glu Asp Leu Lys Lys Leu Ile Asp Leu Glu
    1535                1540                1545
Ser Pro Thr Pro Glu Ser Gln Lys Ser Phe Lys Phe His Ala Leu
    1550                1555                1560
```

-continued

```
Ser Ser Pro Gln Ser Pro Phe Pro Ser Thr Pro Thr Ser Arg Arg
    1565            1570                1575

Ala Leu His Arg Thr Leu Ser Asp Glu Ser Ile Tyr Asn Ser Gln
    1580            1585                1590

Arg Glu His Phe Phe Thr Ser Arg Ala Ser Leu Leu Asp Gln Ala
    1595            1600                1605

Leu Pro Asn Asp Val Leu Phe Ser Ser Thr Tyr Pro Ser Leu Pro
    1610            1615                1620

Lys Ser Leu Pro Leu Arg Arg Pro Ser Tyr Thr Leu Gly Met Lys
    1625            1630                1635

Ser Leu His Gly Glu Phe Ser Ala Ser Asp Ser Ser Leu Thr Asp
    1640            1645                1650

Ile Gln Glu Thr Arg Arg Gln Pro Met Pro Asp Pro Gly Leu Met
    1655            1660                1665

Pro Leu Pro Asp Thr Ala Ala Asp Leu Asp Trp Ser Asn Leu Val
    1670            1675                1680

Asp Ala Ala Lys Ala Tyr Glu Val Gln Arg Ala Ser Phe Phe Ala
    1685            1690                1695

Ala Ser Asp Glu Asn His Arg Pro Leu Ser Ala Ala Ser Asn Ser
    1700            1705                1710

Asp Gln Leu Glu Asp Gln Ala Leu Ala Gln Met Lys Pro Tyr Ser
    1715            1720                1725

Ser Ser Lys Asp Ser Ser Pro Thr Leu Ala Ser Lys Val Asp Gln
    1730            1735                1740

Leu Glu Gly Met Leu Lys Met Leu Arg Glu Asp Leu Lys Lys Glu
    1745            1750                1755

Lys Glu Asp Lys Ala His Leu Gln Ala Glu Val Gln His Leu Arg
    1760            1765                1770

Glu Asp Asn Leu Arg Leu Gln Glu Glu Ser Gln Asn Ala Ser Asp
    1775            1780                1785

Lys Leu Lys Lys Phe Thr Glu Trp Val Phe Asn Thr Ile Asp Met
    1790            1795                1800

Ser
```

<210> SEQ ID NO 5
<211> LENGTH: 66
<212> TYPE: DNA
<213> ORGANISM: Artificial
<220> FEATURE:
<223> OTHER INFORMATION: scRNA
<220> FEATURE:
<221> NAME/KEY: misc_RNA
<222> LOCATION: (1)..(66)
<223> OTHER INFORMATION: shSipa1/1-1

<400> SEQUENCE: 5
gatccgcgtt caagccagga aatagttcaa gagactattt cctggcttga acgtttttta    60
cgcgtg    66

<210> SEQ ID NO 6
<211> LENGTH: 66
<212> TYPE: DNA
<213> ORGANISM: Artificial
<220> FEATURE:
<223> OTHER INFORMATION: scRNA
<220> FEATURE:
<221> NAME/KEY: misc_RNA
<222> LOCATION: (1)..(66)

```
<223> OTHER INFORMATION: shSipa1/1-2

<400> SEQUENCE: 6
gatccgtcca caccgatgac ttctattcaa gagatagaag tcatcggtgt ggattttta      60 cgcgtg                                                                66

<210> SEQ ID NO 7
<211> LENGTH: 63
<212> TYPE: DNA
<213> ORGANISM: Artificial
<220> FEATURE:
<223> OTHER INFORMATION: scRNA
<220> FEATURE:
<221> NAME/KEY: misc_RNA
<222> LOCATION: (1)..(63)
<223> OTHER INFORMATION: shLuc

<400> SEQUENCE: 7
gatccgtgcg ttgctagtac caattcaaga gattggtact agcaacgcac tttttacgc      60 gtg                                                                   63

<210> SEQ ID NO 8
<211> LENGTH: 23
<212> TYPE: DNA
<213> ORGANISM: Artificial
<220> FEATURE:
<223> OTHER INFORMATION: Primer mSipa1/1-F

<400> SEQUENCE: 8
gaaatgactc tgcgaagaaa tgg                                             23

<210> SEQ ID NO 9
<211> LENGTH: 20
<212> TYPE: DNA
<213> ORGANISM: Artificial
<220> FEATURE:
<223> OTHER INFORMATION: Primer mSipa1/1-R

<400> SEQUENCE: 9
ttctacatcc gccacaatgc                                                 20

<210> SEQ ID NO 10
<211> LENGTH: 18
<212> TYPE: DNA
<213> ORGANISM: Artificial
<220> FEATURE:
<223> OTHER INFORMATION: Primer hSipa1/1-F

<400> SEQUENCE: 10
tcgccagggc gctactag                                                   18

<210> SEQ ID NO 11
<211> LENGTH: 21
<212> TYPE: DNA
<213> ORGANISM: Artificial
<220> FEATURE:
<223> OTHER INFORMATION: Primer hSipa1/1-R

<400> SEQUENCE: 11
cccacggagt ttatggttcc t                                               21

<210> SEQ ID NO 12
<211> LENGTH: 20
<212> TYPE: DNA
<213> ORGANISM: Artificial
```

```
<220> FEATURE:
<223> OTHER INFORMATION: Primer mCyclophilin A-F

<400> SEQUENCE: 12
ttttgacttg cgggcatttt                                              20

<210> SEQ ID NO 13
<211> LENGTH: 22
<212> TYPE: DNA
<213> ORGANISM: Artificial
<220> FEATURE:
<223> OTHER INFORMATION: Primer mCyclophilin A-R

<400> SEQUENCE: 13
ggacgctctc ctgagctaca ga                                           22

<210> SEQ ID NO 14
<211> LENGTH: 20
<212> TYPE: DNA
<213> ORGANISM: Artificial
<220> FEATURE:
<223> OTHER INFORMATION: Primer hCyclophilin A-F

<400> SEQUENCE: 14
ttcatctgca ctgccaagac                                              20

<210> SEQ ID NO 15
<211> LENGTH: 20
<212> TYPE: DNA
<213> ORGANISM: Artificial
<220> FEATURE:
<223> OTHER INFORMATION: Primer hCyclophilin A-R

<400> SEQUENCE: 15
tcgagttgtc cacagtcagc                                              20

<210> SEQ ID NO 16
<211> LENGTH: 19
<212> TYPE: DNA
<213> ORGANISM: Artificial
<220> FEATURE:
<223> OTHER INFORMATION: Primer Ap2-F

<400> SEQUENCE: 16
ccgcagacga caggaaggt                                               19

<210> SEQ ID NO 17
<211> LENGTH: 15
<212> TYPE: DNA
<213> ORGANISM: Artificial
<220> FEATURE:
<223> OTHER INFORMATION: Primer Ap2-R

<400> SEQUENCE: 17
agggccccgc catct                                                   15

<210> SEQ ID NO 18
<211> LENGTH: 5919
<212> TYPE: DNA
<213> ORGANISM: Mus musculus

<400> SEQUENCE: 18
gccaccgccg gcaactttgt gagcgagttc agtacgtgcg tgagcgagtg agcggaaagg    60
agagcgcgcg gacgacgcgc ccgggacgcg cggctgcacc gggaagccca ggccaagcgg   120
```

```
ttttgagaga ttgctacaat ttggactcac aagcaagatt tactgcaaac tttgagatgg    180
agtaggtcat atgtcattag tgtggacgct gctgtcttaa gtctgtggcc atggcaccag    240
aacacaggga agcgtgggat tctggtgacc acagagcccc agtgatgcaa gctctactca    300
gtcttaggga ctgaaggaag cctgctgtta gagtgaggca cagggactga aggaagcctg    360
ctgttagagt gaggcacagg gactgttgtg gattacaatg ttttggaaga tctgggttctc   420
tgtcgtctgc aaacaaggca tcatttaacc ttttaaatga aaaggcttaa gatctcaaca    480
ccactgctgt attttctgga agccattctc taaagcagaa gtgcatattt aaaacgcaaa    540
catggtgatc ctttctgcag ggatttaagt gatcgctttt tacatcatga ccagtttgaa    600
gcggtcgcag accgaaagac ctgtcaccgc tgacagagcc tctgttgtca gcacagatgg    660
cgcccccaaa gtccacaccg atgacttcta catgcgtcgc ttccgctctc agaatggcag    720
cctaggatca tcagtcatgg ctgcagtggg gcccctcga agtgaaggcc ctcaccatat     780
cacctcaacc cccggggtcc caagatgggg gttagggca agaatagcag attggcctcc     840
gagaaaggaa aatgtaaaag aatccagccg ttcaagccag gaaatagaaa cctcaagttg    900
ccttgagagc ctgtcctcca aaggcagtcc tgtgagtcag gggagttctg ttagcctcaa    960
ttccaatgac tcagccatgc tgaagagcat acagaacacc ctgaagaaca agacagggcc   1020
agcggagagc atggactcca gattcctcat gcctgaagcc taccccagtt ccccaggaa    1080
agcccttcgc agaattcggc agcgcagcaa cagtgatatc accataagtg agcttgatgt   1140
ggatagcttc gatgaatgta tctccccaac ctacaagtcg gggccatcat tgcacaggga   1200
atatggcagc acatcttcaa tcgacaagca gggaacatcc ggagacagct tcttcgattt   1260
gttaaagggc tataaagatg acagatctga ccgaggtcca actccaacca aactcagtga   1320
cttcctcatc actggtgggg caagggttc tggtttctcc ttggatgtga tcgatggccc    1380
catctcacag agagagaacc tcaggctttt caaggaaagg gaaaaaccac tcaagcgacg   1440
ctctaagtct gagactggag actcgtccat ttttcgtaaa ttgcgcaatg ccaaaggtga   1500
agaactcggg aaatcatcag accttgaaga caacagatca gaagattctg tgaggccctg   1560
gacatgtcca aagtgctttg cccactatga tgtccagagc atattgtttg acttgaatga   1620
agccattatg aacagacata atgtgattaa gaggagaaac accacaacag gagcttcggc   1680
ggctgcggtg gcatccttgg tctccggacc tctgtctcac tcagccagct tcagctctcc   1740
catgggcagc acagaggacc tcaactccaa aggaagcctt ggcatggacc agggagatga   1800
caagagcaat gaactcgtca tgagctgtcc gtattttcgg aatgagattg ggggagaagg   1860
tgagaggaag atcagcctgt ccaagtcgaa ttctggctca tttagtgggt gtgagagcac   1920
atcctttgag tctgccctca gctctcactg caccaacgcg ggcgtggcag ttctcgaagt   1980
gcccaaggaa agcttgatgc tgcatctgga cagggtgaaa aggtacaccg tggaacacgt   2040
ggatcttggc gcatactatt acaggaagtt cttctaccag aaggaacact ggaactattt   2100
tgggctgat gagaacctcg gtccagtggc tgtgagcatt cgaagggaaa accagaagaa    2160
catgaaggaa aacggatctc catacaacta ccgaataata ttcaggacta gtgagctcat   2220
gacgctgagg gggtctgtcc tggaggatgc cattccctcc acggccaagc actcgacagc   2280
caggggattg cctctgaaag aggtgctgga acacgtgatc ccagagctca cgtgcagtg    2340
cctgcgcttg gccttcaaca cacccaaagt cacagagcag ctcatgaaac tggacgagca   2400
agggctgaac tatcagcaga aagtaggcat catgtactgc aaagcaggcc agagcacgga   2460
ggaggagatg tacaacaacg agtctgcagg cccagccttt gaggagttcc ttcagctgct   2520
```

```
gggggaacga gtccggctaa aaggattcga gaagtatcgt gcgcagcttg acaccaaaac   2580
tgactccact ggaacccact ctctgtacac aacctacaaa gactatgaga taatgttcca   2640
cgtctccacc atgctgccct acacacctaa caacaagcaa cagctcctga ggaagcggca   2700
cattgggaat gacattgtga caatagtttt ccaagagcct ggagcacaac cattcagccc   2760
gaaaaacatc cggtctcact ttcagcatgt ttttgtcatt gtccgggctc acaacccttg   2820
cactgagagt gtctgttaca gtgtggcagt caccaggtcc agagatgtac cttcttttgg   2880
acctcccatc cctaaagggg tcaccttccc caagtcaaat gtgttcaggg acttccttt   2940 ggccaaagtg ataaatgcag aaaatgctgc tcataaatca gagaagttcc gggccatggc   3000
gacaaggacc cgccaggaat acctgaaaga tctggcagaa aagaatgtca ccaacacacc   3060
tattgaccct tctggcaagt ttccatttat ttctctggcc tccaagaaga aggaaaagtc   3120
taagccttat ccaggagctg agctcagtag catgggggcc attgtgtggg ctgtccgggc   3180
caaagactac aacaaggcca tggagttcga ctgcctcctt gggatctcca gcagttcat   3240 cgtcctcatt gagcaggaga caaagagtgt ggctttcaat tgctcctgca gagatgtcat   3300
agggtggact tccagcgaca ccagcctcaa aatcttctat gagcggggag aatgtgtgtc   3360
ggtggagagc ttcattagcg gtgaagatat caaagaaatt gtcagaaggc tgcagtttgt   3420
ttcaaaaggt tgtgaatctg tggaaatgac tctgcgaaga aatgggctgg ggcagcttgg   3480
cttccatgtc aactatgagg gcattgtggc ggatgtagaa ccctacggct acgcatggca   3540
agcagggctg aggcagggca gccgcctggt ggagatctgc aaggtagcag tggccaccct   3600
gagccatgaa cagatgatcg atctcttgag aacatcagtc acagtgaagg ttgtcattat   3660
ccctccccat gacgactgca ccccacggag gagttgctca gaaacctacc gcatgccagt   3720
gatggagtac cagatgaatg aaggcatttc ctacgagttc aagtttccct tccggaataa   3780
taacaaatgg cagcggaatg ccagcaaggg tgctcattcg ccccaggttc catctcagct   3840
gcagagtccc atgacctcac gactgaatgc tgggaaggga gatgggaaaa tgccccctcc   3900
agaaagagct gccaacatcc ctcgaagcat ctccagtgac gggcgcccac tggaaaggag   3960
gctgtctcct ggttcggaca tctatgtgac agtctcatcc atggctttgg cgagatccca   4020
gtgccgtaac tctcccagca acttgtcttc gtccagtgag actggctctg gaggtggtac   4080
ctacagacaa aaatccatgc cgaagggttt tggggtgagc cgaagatccc cagcttccat   4140
cgacaggcag aacacccagt cggatataag tggcagtgga aaatccactc ccagctggca   4200
gagaagtgag gacagccttg ccgaccagat ggagccgacg tgccatctcc cagcagtatc   4260
gaaggtactg cctgctttcc gagagagccc cagtgggaga ttgatgcggc aggatccagt   4320
ggttcacttg tctccaaaca aacaaggcca ttctgacagc cactactcca gccactccag   4380
cagcaacacg ctctccagca acgcctcgag tgcacacagt gacgagaagt ggtacgatgg   4440
ggaccgcacg gagtccgacc tcaacagcta caactaccta cagggcacgt ctgccgacag   4500
cgggattgac accgcctcct acggccccag ccatggcagc acggcctccc tgggggcctc   4560
cacatcctca cctcgttcag ggccaggcaa agaaaaggtg gctcccctgt ggcacagctc   4620
cagtgaagtg ctctccctgg cagatcggac cttagagact gagggccacg gcatggacag   4680
gaaagcagag tcctccctga gcctggacat ccacagcaag agccagggcg gtcaagccc   4740 gctgagcagg gagaacagca ccttcagcat aaatgatgct gcgtcccaca ccagtaccat   4800
gagctcccga cactctgcca gcccagtggt attctccagt gccagaagtt cccccaaaga   4860
```

-continued

| | |
|---|---|
| ggagcttcac cccaccgcat cctcccagct cgcaccgtcc ttttcctctt cttcctcatc | 4920 |
| ctcctctgga cctaggactt tctaccctcg ccagggcgcc actagcaaat atctgattgg | 4980 |
| atggaaaaag ccagaaggaa ccattaactc cgtgggattt atggacacac gaaagcgaca | 5040 |
| tcagagtgat ggcaatgaga tagcccacac taggcttcga gcctcaacca gggacctgca | 5100 |
| ggcatcccca agccgacct ccaagtctac cattgaggaa gatctaaaga aactcatcga | 5160 |
| ccttgagagc ccaactcccg aatcccagaa gaatttcaag ttccatgcac tgtcctcccc | 5220 |
| gcagtccccg ttccccacta ccctacctc ccggcgggcc ctgcacagga ctctgtcaga | 5280 |
| tgagagcatt tacagcagcc agagggagca tttcttcacc tccagggctt cgcttctaga | 5340 |
| ccaagccctg cccaacgatg tcctcttcag cagtacctac ccatctctcc ccaagtcact | 5400 |
| tccactgagg aggccatctt acacgttggg aatgaagtca ttgcatggag agttctctgc | 5460 |
| ctcggacagc tccctcaccg acatccagga gacccgaagg cagcctatcc ctgaccctgg | 5520 |
| cctgatgccc ctgcctgatg cagcttcaga ttttggactgg tccaacctag tagatgccgc | 5580 |
| caaagcctat gaggtccaga gagcctcatt ttttgctgct agtgatgaaa accatcgccc | 5640 |
| cctgagcgcg gcctccaaca gtgaccagct ggaggagcag gccctggtcc agatgaagtc | 5700 |
| ctacagcagg ttggtcaccc ggtgctgagg tcatgaatgt acaccatgtg tctcctcagt | 5760 |
| agtgccagac gtgatgaaga ggagatggaa ggccattgat gagctggaag ctcaacagcc | 5820 |
| atgccagaca cttgatttta gatagaatac cttacaacta actactggaa atacaattaa | 5880 |
| actggtcttg atggcttaag gataaaaaaa aaaaaaaa | 5919 |

<210> SEQ ID NO 19
<211> LENGTH: 1340
<212> TYPE: DNA
<213> ORGANISM: Mus musculus

<400> SEQUENCE: 19

| | |
|---|---|
| caaacatgta tctggcaaga atttaaaggc cacctcttgt gtaatttgtg gaatgctgga | 60 |
| aaaggatcct ctgcctctct cctcaggatg tgcgcaccca tgcaggattc tgtgctcagg | 120 |
| ctctgtgcct gctgcctcct gcctgacgag ctcggggagga agttcgtctt cctgtccatc | 180 |
| acctgggaag gatggtaacc gttctctgta atctggtgga ggatatggag ccagctgccc | 240 |
| tgagcagtat tttgtttctg ttgtcgtcgt cgttgtggtc gtcttcataa attagcactg | 300 |
| atggggtgga ggaggctgct ctgcttaagg aactgcaggc attttgtgaa ttagtgaaag | 360 |
| acttccagct ctgagagtag atgaaagtca ggtgagcttg ggaaaaggtg gccgtgagtg | 420 |
| ccgggcttcc tctgcagtgt tctctgtgtg ggtaagtaag acctcaggta ctctggctcc | 480 |
| gggaaagagt gctcgatttc tgtgtgctct gtatatttgc tcttgccgac tatgacaagc | 540 |
| ttttgtaggg aaataagtat caatttgaaa aatgaaacgt tttaaaaagt gagtgttgta | 600 |
| gcataatcaa taaagtcttg ttcagttttt agtgttctca gaatgccccc ctgcattgct | 660 |
| ctaattatct gattaggttg gtcaaacttg tggtcagcac agtggcatga tgtctccatt | 720 |
| cctagaggtc ctgggtgccg aagtctgtac ttccctccca gcttaggaaa caattcagct | 780 |
| aaacagaagt agtcatagcg cctctttcaa tgttaactga tgggttctat taactttttt | 840 |
| attttttcctt tatatctgct ttattaaaaa tgtagatttt agatccgtgt gccacaattc | 900 |
| agtattgagt ctcttttca tgtgcctgat tttgactggt gcatatttat tttaggtatg | 960 |
| cttgtcaaat gctaatttca tgttgtcctc ctctctttag gggaagcgtg ggattctggt | 1020 |
| gaccacagag ccccagtgat gcaagctcta ctcagtctta gggactgaag gaagcctgct | 1080 |

```
gttagagtga ggcacaggga ctgaaggaag cctgctgtta gagtgaggca cagggactgt    1140
tgtggattac aatgtttgga agatctgggt tctctgtcgt ctgcaaacaa ggcatcattt    1200 aacctttaa atgaaaaggc ttaagatctc aacaccactg ctgtattttc tggaagccat    1260
tctctaaagc agaagtgcat atttaaaacg caaacatggt gatcctttct gcagggattt    1320
aagtgatcgc ttttacatc                                                1340
```

USE OF SIRNA TARGETTING SIPA1L1 FOR THE REDUCTION OF ADIPOGENESIS

The present invention concerns Sipa1l1 a new target involved in adipogenesis modulation as well as screening test for identification of modulators of the activity of this target. Further, the present invention relates to modulators of Sipa1l1 activity and their use, especially in pharmaceutical composition, to modulate adipogenesis and thus treat obesity and related disorders.

Obesity is a major risk factor for a number of disorders including hypertension, coronary artery disease, dyslipidemia, insulin resistance and type 2 diabetes. Because of the importance of the obesity epidemic, a great deal of investigation has centered on the biology of the adipocyte, including the developmental pathway by which new adipocytes are created. Adipogenesis is the process by which undifferentiated mesenchymal precursor cells become mature adipocytes. Throughout the last decade considerable progress has been made in elucidating the molecular mechanisms of adipocyte differentiation, which involve sequential activation of transcription factors from several families such as CCAAT/enhancer binding proteins (C/EBPα, α, and γ) and the nuclear hormone receptor peroxisome proliferator-activated receptor γ (PPARγ) (Rosen, E. D. et al., 2002). PPARγ is described as a "master regulator" of adipogenesis since it has been shown to be both sufficient and necessary for adipogenesis both in vitro and in vivo. Recently, new transcription factors have been described to participate in adipogenesis such as KLF family (KLF2, 5 and KLF15) (Banerjee, S. S. et al., 2003; Gray, S. M. et al., 2002), Ebf family (Jimenez, M. A. et al., 2007) and Krox 20 (Chen, Z. et al., 2005), suggesting that the transcriptional cascade occurring during adipogenesis is much more complex than previously thought. Furthermore, signaling molecules and/or receptors such as the Wnt family of secreted proteins (Kang S. et al., 2007), sonic hedgehog protein, Notch receptor have also been described to be involved in molecular events leading to adipocyte formation. It is interesting to note that extracellular and intracellular events are somehow coupled to regulate adipogenesis. All these signaling pathways converge on a tightly regulated transcriptional cascade, which needs to be more completely understood to potentially control adipocyte development and prevent obesity.

Storage of fat in adipose tissue is limited and exceeding this capacity leads to accumulation of lipids in others tissues, in particular muscle, liver, and the endocrine pancreas, and to the secretion by adipocytes of various adipokines. The adipose tissue consists of several deposits located at different anatomical sites which may originate from distinct precursors and which have different physiological functions and pathophysiological roles. The visceral, as opposed to the subcutaneous adipose depots, may contribute more to the defects associated with the metabolic syndrome.

Cannabinoid 1 receptors have been identified in all organs playing a key role in glucose metabolism and type 2 diabetes, i.e. adipose tissue, the gastrointestinal tract, the liver, the skeletal muscle and the pancreas. Rimonabant, the first selective cannabinoid receptor 1 (CB1R) antagonist in clinical use, has been shown to reduce food intake and body weight thus improving glucose metabolism regulation.

However, there is still a need for novel therapeutic targets for the treatment of obesity.

Spa1 mouse protein is known to hamper mitogen-induced cell cycle progression when abnormally or prematurely expressed. The human Sipa1 gene was cloned in 1997; it encodes a 1042-amino acid polypeptide with a predicted mass of 130 kD. The protein contains a C-terminal leucine zipper motif and an N-terminal GTPase activating protein (GAP) domain homologous to the human RAP1GAP protein (Tsai, I. C. et al., 2007). Human and mouse Spa1 amino acid sequences are 90% identical, with their GAP domains 98% identical. Human SPA1 was expressed at high levels in lymphohematopoietic tissues and at lower levels in several other tissues. Sipa1l1 belongs to the Rap/Ras GTPase activating protein family and has been described as an anti-apoptotic protein by acting on p53 expression. This protein has a PDZ domain and can potentially bind to transcription factors and modulate their action on gene transcription.

The inventors have now found that Sipa1l1 plays a critical role in adipocyte differentiation. Sipa1l1 might modify gene expression by acting on cofactors or intermediate signaling proteins. It is a now considered as a new relevant target for modulation of adipogenesis, and thus for the treatment of obesity and related disorders.

DETAILED DESCRIPTION OF THE INVENTION

The present invention consists in the use of inhibitors of Sipa1l1 activity for modulation of adipogenesis, in particular for treatment of obesity and related disorders. The invention also concerns pharmaceutical composition containing such modulators of adipogenesis and related disorders and screening test for such modulators.

There is a need for new therapeutic targets useful to regulate adipogenesis and to treat obesity and related disorders. The inventors have now identified le role of Sipa1l1 in adipogenesis modulation.

Through a transcriptomic approach, they identified genes whose expression was correlated with body weight gain in cohorts of C57BI/6 mice fed a high fat diet. Then, they conducted a second analysis in order to evaluate the changes in gene expression induced by rimonabant treatment of the high fat diet fed mice. Genes which have never been described before in adipocyte biology, but which might be involved in important biological processes such as signaling, modification of extracellular matrix proteins, and gene transcription were retained. These genes could be important for adipogenesis especially since they might be involved in the mechanism by which rimonabant reduces fat mass in mice. In this context, Sipa1l1 was identified as involved in adipocytes metabolism, especially in new signaling pathway. More generally, this gene appears to play a role in adipogenesis and control of adipose tissue development in obesity.

The present invention consists in identification of modulators of Sipa1l1 activity. Such modulators can be any compound or molecule able to modulate Sipa1l1 activity in particular small molecules, lipids and siRNA.

Modulators of Sipa1l1 activity can be identified by detecting the ability of an agent to modulate the activity of Sipa1l1. Inhibitors of Sipa1l1 are any compound able to reduce or inhibit, totally or partially, the activity of Sipa1l1. Inhibitors of Sipa1l1 include, but are not limited to, agents that interfere with the interaction of Sipa1l1 with its natural ligand in the intracellular compartment, agents that reduce Sipa1l1 expression, both at transcriptional and translational levels, as well as agents that inhibit intracellular signals wherein Sipa1l1 is involved.

In one embodiment, Sipa1l1 activity can be reduced using small molecules that inhibit, totally or partially, the transcription of Sipa1l1. Such modulators can be identified using methods well known by the person skilled of the art, as a reporting system consisting in the promoter of Sipa1l1 linked in frame to a reporter gene and expressed in a suitable cell line; the reporter gene product's activity can be quantitatively measured. Thus, a compound that inhibits the expression of the reporter gene, for example by inhibiting an activating transcription factor, can be considered as a potential candidate.

The reporter genes that can be used in such reporting systems are numerous and well known in the art. For example, such reporter genes can be genes allowing expression of Green Fluorescent Protein (GFP), luciferase, β-galactosidase . . . .

Therefore, on aspect of the present invention is to provide a method for screening for inhibitors of the activity of Sipa1l1 which comprises the steps of:
a) transfecting a cell line with a reporter construction comprising a Sipa1l1 promoter linked to a reporter gene,
b) cultivating said cell line in condition to allow expression of the reporter gene,
c) adding candidate compounds into the cell culture,
d) identifying inhibitor compounds as being those compounds which have the ability to reduce or inhibit the reporter gene expression.

The predicted promoter of Sipa1l1 to be used in the described above screening test for modulators of Sipa1l1 transcription corresponds to SEQ ID NO. 19.

In another embodiment, the expression of Sipa1l1 is modulated through RNA interference, using small interfering RNAs (siRNA) or small hairpin RNAs (shRNAs). Therefore, in one aspect, the present invention relates to double stranded nucleic acid molecules including small nucleic acid molecules, such as short interfering nucleic acid (siNA), short interfering RNA (siRNA), double-stranded RNA (dsRNA), micro-RNA (miRNA), and short hairpin RNA (shRNA) molecules able to mediate RNA interference (RNAi) against Sipa1l1 gene expression, including cocktails of such small nucleic acid molecules and suitable formulations of such small nucleic acid molecules.

The phenomenon of RNAi mediated gene silencing has been described first in the *Caenorhabditis elegans* system, in which microinjection of long double stranded RNA molecules was reported. The mechanism of RNA mediated gene inactivation seems to be slightly different in the various organisms that have been investigated so far. However, in all systems, RNA mediated gene silencing is based on post-transcriptional degradation of the target mRNA induced by the endonuclease Argonaute2 which is part of the so called RISC complex. Sequence specificity of degradation is determined by the nucleotide sequence of the specific antisense RNA strand loaded into the RISC complex.

The introduction into cells of a siRNA compound results in cells having a reduced level of the target mRNA and, thus, of the corresponding polypeptide and, concurrently, of the corresponding enzyme activity.

SiRNAs specific for Sipa1l1, as described herein, can be used as modulators of Sipa1l1 activity, in order to reduce the translation of Sipa1l1 mRNA. More particularly, siRNA specific for Sipa1l1 can be used to reduce adipogenesis and thus to treat obesity and related diseases.

In one embodiment, the invention features a double stranded nucleic acid molecule, such as an siRNA molecule, where one of the strands comprises nucleotide sequence having complementarity to a predetermined Sipa1l1 nucleotide sequence in a target Sipa1l1 nucleic acid molecule, or a portion thereof.

The RNA molecule can be used modified or unmodified. An example of modification is the incorporation of tricyclo-DNA to allow improved serum stability of oligonucleotide.

In one embodiment, the predetermined Sipa1l1 nucleotide sequence is a Sipa1l1 nucleotide target sequence described herein (SEQ ID NO. 1 and SEQ ID NO. 3).

Due to the potential for sequence variability of the genome across different organisms or different subjects, selection of siRNA molecules for broad therapeutic applications likely involves the conserved regions of the gene. Thus in one embodiment, the present invention relates to siRNA molecules that target conserved regions of the genome or regions that are conserved across different targets. SiRNA molecules designed to target conserved regions of various targets enable efficient inhibition of Sipa1l1 gene expression in diverse patient populations.

In one embodiment, the invention features a double-stranded short interfering nucleic acid molecule that down-regulates expression of a target Sipa1l1 gene or that directs cleavage of a target RNA, wherein said siRNA molecule comprises about 15 to about 28 base pairs, preferably 19 base pairs. A siRNA or RNAi inhibitor of the instant invention can be chemically synthesized, expressed from a vector or enzymatically synthesized.

In a particular embodiment, the siRNA specific for Sipa1l1 are shRNA having sequence SEQ ID NO. 5 or SEQ ID NO. 6. In a preferred embodiment, the siRNA specific for Sipa1l1 is shRNA having sequence SEQ ID NO. 6.

The use of a siRNA according to the present invention leads to reduction of the mRNA level from 5% to 20%, preferably from 5% to 15%, more preferably from 5% to 10% of the mRNA level of the corresponding wild type cell. The wild type cell is the cell prior to the introduction of the nucleic acid encoding the siRNA compound, in which the targeted mRNA is not degraded by a siRNA compound.

Inhibitors of Sipa1l1 activity can be administered by any suitable route, both locally or systemically depending on the nature of the molecule and the expected effect. SiRNA can be administrated locally in case of double strand molecule directly in the targeted tissue, or administrated through a vector in case of shRNA, according to protocols used in the art.

In one embodiment, RNAi is obtained using shRNA molecules. ShRNA constructs encode a stem-loop RNA. After introduction into cells, this stem-loop RNA is processed into a double stranded RNA compound, the sequence of which corresponds to the stem of the original RNA molecule. Such double stranded RNA can be prepared according to any method known in the art including in vitro and in vivo methods as, but not limited to, described in Sadhu et al (1987), Bhattacharyya et al, (1990) or U.S. Pat. No. 5,795,715.

For in vivo administration, shRNA can be introduced into a plasmid. Plasmid-derived shRNAs present the advantage to provide the option for combination with reporter genes or selection markers, and delivery via viral or non viral vectors. The introduction of shRNA into a vector and then into cells ensure that the shRNA is continuously expressed. The vector is usually passed on to daughter cells, allowing the gene silencing to be inherited.

The present invention also provides vectors comprising the polynucleotides for expression of shRNA expression of the invention. These vectors are for example AAV vector, retroviral vector in particular lentiviral vector, adenoviral vector which can be administered by different suitable routes including intravenous route, intramuscular route, direct injection into subcutaneous tissue or other targeted tissue chosen according to usual practice.

The route of administration of siRNA varies from local, direct delivery to systemic intravenous administration. The advantage of local delivery is that the doses of siRNA required for efficacy are substantially low since the molecules are injected into or near the target tissue. Local administration also allows for focused delivery of siRNA. For such direct delivery, naked siRNA can be used. "Naked siRNA" refers to delivery of siRNA (unmodified or modified) in saline or other simple excipients such as 5% dextrose. The ease of formulation and administration of such molecules makes this an attractive therapeutic approach. Naked DNA can also be formulated into lipids especially liposomes.

Systemic application of siRNA is often less invasive and, more importantly, not limited to tissues which are sufficiently accessible from outside. For systemic delivery, siRNA can be formulated with cholesterol conjugate, liposomes or polymer-based nanoparticles. Liposomes are traditionally used in order to provide increased pharmacokinetics properties and/or decreased toxicity profiles. They allow significant and repeated success in vivo delivery. Currently, use of lipid-based formulations of systemic delivery of siRNA, especially to hepatocytes, appears to represent one of the most promising near-term opportunities for development of RNAi therapeutics. Formulation with polymers such as dynamic polyconjugates—for example coupled to N-acetylglucosamine for hepatocytes targeting—and cyclodextrin-based nanoparticles allow both targeted delivery and endosomal escape mechanisms. Others polymers such as atelocollagen and chitosan allow therapeutic effects on subcutaneous tumor xenografts as well as on bone metastases.

SiRNA can also be directly conjugated with a molecular entity designed to help targeted delivery. Given the nature of the siRNA duplex, the presence of the inactive or sense stand makes for an ideal site for conjugation. Examples of conjugates are lipophilic conjugates such as cholesterol, or aptamer-based conjugates.

Cationic peptides and proteins are also used to form complexes with the negatively charged phosphate backbone of the siRNA duplex.

These different delivery approaches can be used to target the Sipa1l1 siRNA into the relevant tissue, especially adipose tissue. For such targeting, siRNA can be conjugated to different molecules interacting with pre-adipocytes and adipocytes, as for example ligands interacting with lipids transporters, receptors, insulin receptor or any molecule known in the art.

Another object of the invention is a pharmaceutical composition, which comprises, as active principle, a modulator of Sipa1l1 according to the present invention. These pharmaceutical compositions comprise an effective dose of at least one modulator according to the invention, and at least one pharmaceutically acceptable excipient. Said excipients are chosen according to the pharmaceutical form and the administration route desired, among usual excipients known of one of skill in the art.

The invention also consists in a method for modulation of adipogenesis. Such method can be used to treat obesity or related diseases. Such method can also be used in order to decrease fat accumulation in a cosmetic purpose.

Modulators of Sipa1l1 activity are useful in therapeutics to modulate adipogenesis, in particular in the treatment and prevention of obesity related disorders, in particular type 2 diabetes, dyslipidemia, elevated blood pressure, insulin resistance, cardiovascular disorders and more generally metabolic syndromes.

The present invention, according to another of its aspects, relates to a method for the treatment of the above pathologies, which comprises the in vivo administration to a patient of an effective dose of a modulator of Sipa1l1 according to the invention.

The appropriate unitary dosage forms comprise the oral forms, such as tablets, hard or soft gelatin capsules, powders, granules and oral solutions or suspensions, the sublingual, buccal, intratracheal, intraocular, intranasal forms, by inhalation, the topical, transdermal, sub-cutaneous, intramuscular or intra-venous forms, the rectal forms and the implants. For the topical application, the compounds of the invention may be used as creams, gels, ointments or lotions.

According to usual practice, the dosage suitable to each patient is determined by the physician according to the administration route, the weight and response of the patient.

Sipa1l1 inhibitors are also useful for cosmetic applications in order to reduce disgraceful fat accumulation. For cosmetic applications, inhibitors of Sipa1l1 can be incorporated in a suitable formulation for topical use. The inhibitors of Sipa1l1 can both be small molecules or siRNA as previously described.

The invention is now described by reference to the following examples, which are illustrative only, and are not intended to limit the present invention.

MATERIAL AND METHODS

Animals' Treatment

Figure 1A:
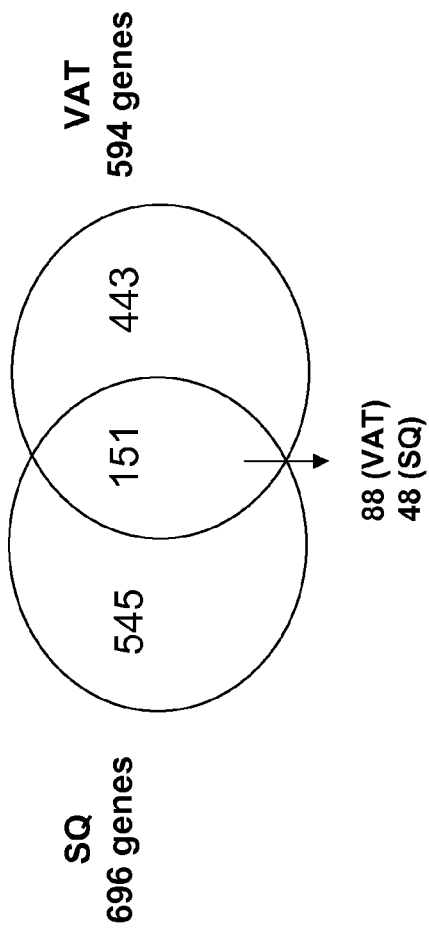
FIG. 1: Selection of critical adipose tissue regulatory genes. The Venn diagrams illustrate the selection of genes based on the following criteria. 1) Similar regulation by high fat feeding in subcutaneous (SCAT or Sq) and visceral (VAT). 151 genes were selected (48 for SCAT and 88 for VAT). 2) Among those 151 genes, selection of genes regulated by rimonabant treatment (14 for SCAT and 54 for VAT). This led to the selection of 34 genes regulated in both tissues by high fat feeding and rimonabant. Among those genes, 16 have expression level correlated with body weight of L, M and H groups (obesity-linked) and 18 are regulated by HFD to the same level in each subgroup (not obesity-linked).

C57BL/6J mice, which are obesity-prone (Collins S. et al., 2004) were fed for 6 months with a high fat diet (HFD). After 6 months of HFD, mice exhibited scattered body weights with various degrees of glucose intolerance (measured by a glucose tolerance test. The HFD mice were separated into 3 groups displaying the same level of glucose intolerance but with low (L), medium (M) or high (H) body weights and treated them, as well as normal chow (NC) fed mice, for one month with vehicle or Rimonabant (10 mg.kg$^{-1}$.day$^{-1}$), to normalize their body weight. The treatment also normalized glucose tolerance, as described previously (Poirier et al., 2005).

RNA Preparation, Labelling and Hybridization on cDNA Microarrays.

RNA from 5 different mice per group was extracted from visceral and subcutaneous adipose tissues using peqGOLD Trifast™ (peqlab) and chloroform-isoamylalcool (24:1) extraction. RNA was precipitated with isopropanol and purified by passage over RNeasy columns (Qiagen). RNA quality was checked before and after amplification with a Bioanalyzer 2100 (Agilent). RNA was reverse transcribed and RNA was amplified with MessageAmp™ kit (Ambion). A Mouse Universal Reference (Clontech) was similarly amplified and both adipose tissue and reference RNAs were labeled by an indirect technique with Cy5 and Cy3 according to published protocols (de Fourmestraux et al., J. Biol. Chem. 2004 279: 50743-53). Labeled RNAs were hybridized to microarrays containing 17664 cDNAs prepared at the DNA Array Facility of the University of Lausanne. Scanning, image, and quality control analyses were performed as previously published (de Fourmestraux et al., J. Biol. Chem. 2004 279:50743-53). Data were expressed as log$_2$ intensity ratios (Cy5/Cy3), normalized with a print tip locally weighted linear regression (Lowess) method and filtered based on spot quality and incomplete annotation. All analyses were performed with the R software for statistical computing available at the Comprehensive R Archive Network (cran.us.r-project.org/).

Cell Culture

3T3-L1 cells were cultured in DMEM (Gibco) with 10% FBS (Gibco) at 5% $CO_2$. After retroviral infection (see below), cells were allow to grow to confluence in either 100-mm or 60-mm dishes in DMEM with 10% FBS. Once confluence was reached, cells were exposed to differentiation medium containing dexamethasone (1 µM), insulin (5 µg/ml), and isobutylmethylxanthine (0.5 µM) (DMI). After 2 days cells were maintained in medium containing insulin (5 µg/ml) until ready for harvest at 7 days.

Oil-Red-O Staining

After 7 to 10 days of differentiation, cells were washed once in PBS and fixed with formaldehyde (Formalde-fresh; Fisher) for 15 minutes. The staining solution was prepared by dissolving 0.5 g oil-red-O in 100 ml of isopropanol; 60 ml of this solution was mixed with 40 ml of distilled water. After 1 hour at room temperature the staining solution was filtered and added to dishes for 4 hours. The staining solution was then removed and cells were washed twice with distilled water.

shRNA Constructs

ShRNAs were constructed using the RNAi-Ready pSIREN-RetroQ ZsGreen (Clontech). Target sequences for Sipa1l1 were designed by querying the Whitehead siRNA algorithm (http://jura.wi.mit.edu/bioc/siRNAext/) as well as the siRNA designer software from Clontech (http://bioinfo.clontech.com/rnaidesigner/); at least two sequences represented by both algorithms were subcloned into the pSIREN vectors (Clontech) using the EcoRI and BamH1 restriction sites. The following target sequences for Sipa1l1 were chosen SEQ ID NO. 18. As a negative control, we used the following siRNA sequence against luciferase: SEQ ID NO. 7.

Transfection of shRNA Constructs

The specificity of shRNAs was tested in 293T HEK cells co-transfected using calcium-Phosphate methods described in Jordan M. et al (2004) with expression vectors containing Sipa1l1 cDNA and the RNAi-Ready pSIREN-RetroQ ZsGreen vector expressing either the shRNA against lucifeare (control shLUC) or Sipa1l1. RT-PCR analysis was performed on cell RNA-extraction 24 h after transfection.

Generation of Retro Viral Constructs and Retro Viral Infections

Retroviruses were constructed in the RNAi-Ready pSIREN-RetroQ ZsGreen (pSIREN Clontech) or pMSCV puromycin plasmid (pMSCV, Clontech). Viral constructs were transfected using calcium-phosphate method described in Jordan M. et al (2004) into 293 HEK packaging cells along with constructs encoding gag-pol and the VSV-G protein. Supernatants were harvested after 48 h in presence of 3 µm of Trichostatin A (Sigma) and either used immediately or snap frozen and stored at −80° C. for later use. Viral supernatants were added to the cells for 6 hours in the presence of polybrene (4 µg/ml) and diluted two times with fresh medium for the next 15 hours.

Isolation of Adipocytes and Stromal Vascular Fraction (SVF) from Adipose Tissue

Eight week-old male C57BL/6J mice (n=6-8) were euthanized by $CO_2$ inhalation and epididymal (visceral) and subcutaneous adipose tissue were collected and placed in DMEM medium containing 10 mg/mL fatty acid-poor BSA (Sigma-Aldrich, St. Louis, Mich.). The tissue was minced into fine pieces and then digested in 0.12 units/mL collagenase type I (Sigma) at 37° C. in a shaking water bath (80 Hz) for 1 hour. Samples were then filtered through a sterile 250 µm nylon mesh (Scrynel NY250HC, Milian) to remove undigested fragments. The resulting suspension was centrifuged at 1100 RPM for 10 min to separate SVF from adipocytes. Adipocytes were removed and washed with DMEM buffer. They were then suspended in peqGOLD TriFast reagent (Axonlab) and RNA was isolated according to the manufacturer's instructions. The SVF fraction was incubated in erythrocyte lysis buffer (0.154 mM $NH_4Cl$, 10 mM $KHCO_3$, 0.1 mM EDTA) for 2 min. Cells were then centrifuged at 1100 RPM for 10 min and re-suspended in 500 µl of peqGOLD TriFast reagent (Axonlab) for RNA isolation.

RNA Extraction and Real-Time PCR

Total RNA was isolated from cultured cells using peqGOLD TriFast reagent according to the manufacturer's instructions (Axonlab). First strand cDNA was synthesized from 0.5 µg of total RNA using random primers and Superscript II (Invitrogen). Real time PCR was performed using Power SYBR Green Mix (Applied Biosystem). The following primers were used for mouse genes: SEQ ID NO. 8

(mSipa1l1-F), SEQ ID NO. 9 (mSipa1l1-R), SEQ ID NO. 16 (Ap2-F), SEQ ID NO. 17 (Ap2-R), SEQ ID NO. 12 (mCyclophilin A-F) and SEQ ID NO. 13 (mCyclophilin A-R). The following primers were used for human genes: SEQ ID NO. 10 (hSlap1l1-F), SEQ ID NO. 11 (hSlap1l1-R), SEQ D NO. 14 (hCyclophilin A-F) and SEQ ID NO. 15 (hcyclophilin A-R).

Northern Blot

Total RNA from various mouse tissues was isolated using the peqGOLD TriFast reagent according to the manufacturer's instructions (Axonlab). Total RNA (8 µg) was separated on a 1.2% agarose/forlmaldehyde gel and transfected overnight to a nylon membrane. To control for RNA quantity loading, the membrane was stained with methylene blue prior the subsequent hybridizations. For the detection of Sipa1l1 signals, probes from the full-length cDNA mouse plasmid (Open Biosystem) were used. The probes were labeled by random priming with [$\alpha$-$^{32}$P]dCTP (Amersham). Hybridization and washing were carried out using the Quickhib method according to manufacturer's instructions (Stratagene). Blots were exposed to Hyperfilm ECL (Amersham) at −80° C. for 1 day or several days depending on the signal intensity.

Results

Example 1

Microarray Results

Figure 1B:
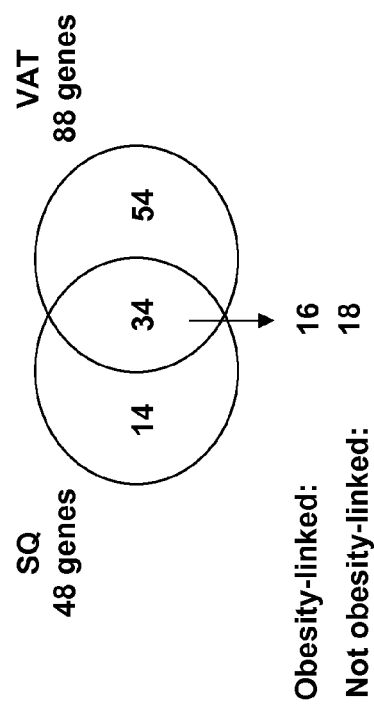

Bioinformatic analysis of the microarray data was performed to identify genes that fulfilled the three following criteria: (i) regulated by high fat feeding, (ii) similar regulated expression by high fat feeding in both visceral (VAT) and subcutaneous fat (SCAT) and (iii) similar normalization of their expression by rimonabant treatment (FIG. 1). Out of the ~17,000 gene targets present on the cDNA microarray used, 34 genes fulfilled these criteria, which are listed in Table 1. Remarkably, 10 of these genes—Cav1, Fgf1, Fndc3b, Kif5b, Mest, Npr3, Pik3ca, Sparc, Vldlr, and Wwtr1—were previously known to be important regulators of adipose tissue development and function. Some of these genes had expression levels correlated with body weight gain (shown in grey in Table 1), suggesting a potential role in hyperplasia and/or hypertrophy of adipose tissues during obesity. These results validate the approach used to identify possible novel targets for therapeutic treatment of obesity.

Most importantly, many of the genes cited in table 1 have never been studied in the context of adipose tissue development or biology. These genes belong to the following classes of function: extracellular matrix/cell interaction, cytoskeleton, intracellular signaling, enzymes, and transcription factors/co-factors. They are likely involved in tissue remodeling, and particularly in adipocyte development. One of these genes, Sipa1l1 gene and it role in adipocyte biology, is presented herein and constitutes one aspect of the present invention.

Sipa1l1 belongs to the Rap/Ras GTPase activating protein family and has been described as an anti-apoptotic protein by acting on p53 expression (Tsai I. C. et al., 2007). This protein has also a PDZ domain and can potentially bind to transcription factors and modulate their action on gene transcription.

TABLE 1

List of 34 gene candidates regulated by HFD and rimonabant in SCAT and VAT. The full name and gene symbol are showed in the first column. The biological role for known genes and references are indicated in the second column. All these genes were up-regulated by HFD and normalized by rimonabant treatment, excepted for Plac8 and Rp9h, which were down-regulated by HFD. The genes correlated to body weight increase are shown in italic.

| Gene name | Biological function and references |
|---|---|
| *Acetyl-Coenzyme A dehydrogenase, medium chain (Acadm)* | |
| ARP2 actin-related protein 2 homolog (Actr2) | |
| Amyloid beta (A4) precursor protein (App) | |
| Annexin A2 (Anxa2) | Role in actin-assembly |
| Calmodulin 1 (Calm1) | |
| Caveolin, caveolae protein 1 Cav1) | Role in lipid homeostasis |
| Cyclin G1 (Ccgn1) | |
| Cold shock domain containing E1 (Csde) | |
| Expressed sequence AW112037 | |
| Fibroblast growth factor 1 (Fgf1) | Regulator of human adipogenesis |
| Fibronectin type III domain containing 3B (Fndc3b) | Role in adipogenesis |
| Kinesin family member 5B (Kif5b) | Role in insulin-stimulated GLUT4 translocation to the plasma membrane |
| *Mesoderm specific transcript (Mest)* | Adipocyte differentiation and enlargement |
| Nucleosome assembly protein 1-like 1 (Nap1L1) | |
| Nidogen 1 (Nid1) | |
| *natriuretic peptide receptor 3 (Npr3)* | Possible role in sodium retention characteristic of obesity associated hypertension |
| nuclear undecaprenyl pyrophosphate synthase 1 homolog (Nus1) | |
| *Phosphatidylinositol 3-kinase, catalytic, alpha polypeptide (Pik3ca)* | Essential for proper growth factor signaling. Role in adipogenesis. |
| Placenta-specific 8 (Plac8) | |
| Pleckstrin homology domain containing, family C (Plekhc1) | |
| Protein tyrosine phosphatase 4a1 (Ptp4a1) | Implicated in cell growth, differentiation, and tumor invasion. |
| Related RAS viral (Rras2) oncogene homolog 2 | |
| Retinitis pigmentosa 9 homolog (Rp9h) | |
| *Secreted acidic cysteine rich glycoprotein (Sparc)* | Mediates cell-matrix interactions and play a differentiation and angiogenesis. |
| Signal-induced proliferation-associated 1 like 1 (Sipa1l1) | |
| *Spectrin beta 2 (Spnb2)* | |
| ST3 beta-galactoside alpha-2,3-sialyltransferase 6 (St3gal6) | |
| Vestigial like 3 (Vgll3) | |
| Very low density lipoprotein receptor (Vldlr) | Involved in lipolysis |
| *Zinc finger, DHHC domain containing 2 (Zdhhc2)* | |
| WD repeat domain 26 (Wdr26) | |
| WW domain containing transcription regulator 1 (Wwtr1) | Regulates mesenchymal stem cell differentiation |
| *Expressed sequence AW112037* | |
| *RIKEN cDNA B930093H17 gene (like-glycosyltransferase)* | |

Example 2

Tissue and Cellular Expression of the Selected Genes

To better understand the role of Sipa1l1 in adipocytes development, its pattern of expression was first characterized.

mRNA levels were measured by northern-blot and RT-PCR in various mouse tissues, in isolated preadipocytes and adipocytes, in visceral adipose tissue (VAT) and subcutaneous adipose tissue (SCAT) of mouse obesity model (Ob/Ob mice) and in human adipose tissues.

Figure 2B:
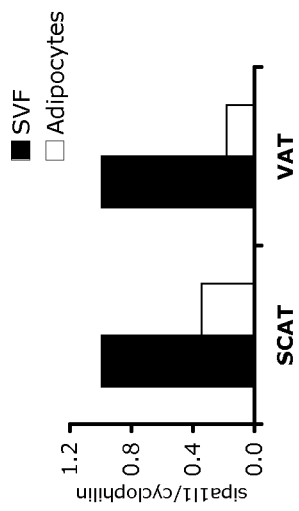
FIG. 2: Sipa1l1 expression in various tissue and cell types. A) Northern Blotting for Sipa1l1 showing mRNA expression in various mouse tissues: spleen, muscle (gastrocenemius), heart, lung, kidney, liver, brown adipose tissue (BAT), sub-cutaneous (SCAT) and visceral (VAT) adipose tissues. As a control the membrane is stained with methylene blue. The size of Sipa1l1 mRNA is shown on the right. mRNA levels of Sipa1l1 measured by RT-PCR B) in SCAT and VAT of wild-type and Ob/Ob mice (n=5) p<0.05, data are shown as mean±sd and expressed as fold increase relative to the control SCAT set at 1. C) in SVF and isolated adipocytes of mice (n=5 mice pooled for each extraction, experiment was repeated 3 times, a representative experiment is shown). Data are expressed as fold increase relative to SCAT SVF expression. D) in human whole tissue SCAT and VAT, isolated adipocytes, isolated preadipocytes and adipocytes differentiated in vitro. Data are expressed as levels relative to whole tissue SCAT expression set arbitrary at 1. E) in 3T3-L1 cells prior DMI treatment day-2 and after DMI treatment until day 7. N=2-3 sets of cells. Data are represented as levels relative to the expression at day 0.

By northern-blotting, it was shown that Sipa1l1 mRNA was expressed at high level in kidney and showed a weaker expression in all adipose tissues, and at very low level in lung (signals at 5 and 1.5 kb indicated by arrows on FIG. 2A), whereas no expression is observed in other tissues (spleen, muscle, heart, liver) (FIG. 2A). The expression patterns of Sipa1l1 were then observed by RT-PCR. In white adipose tissues of Ob/Ob mice, Sipa1l1 level is increased compared to level in wild type mice (FIG. 2B). Values are expressed as fold increase relative to the control values in SCAT set arbitrarily at 1.

Figure 2C:
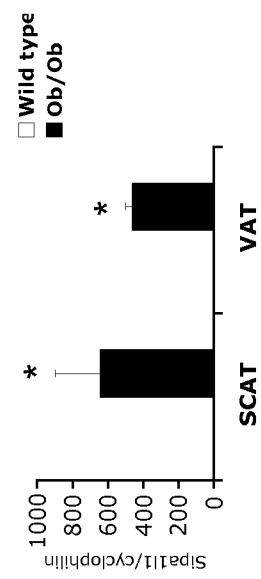

Adipose tissue is a complex tissue that includes not only mature adipocytes, but also precursor cells such as preadipocytes as well as blood vessels, macrophages and fibroblastic cells. Based on a collagenase I digestion technique, stromal vascular fraction (SVF) (including preadipocyte, endothelial and macrophage cells) was separated from the isolated adipocyte fraction. It was found that Sipa1l1 is predominantly expressed in the stromal vascular fraction, containing preadipocytes (FIG. 2C). These results indicate that Sipa1l1 is more expressed in preadipocytes and thus appears to be involved in differentiation or proliferation processes.

Figure 2D:
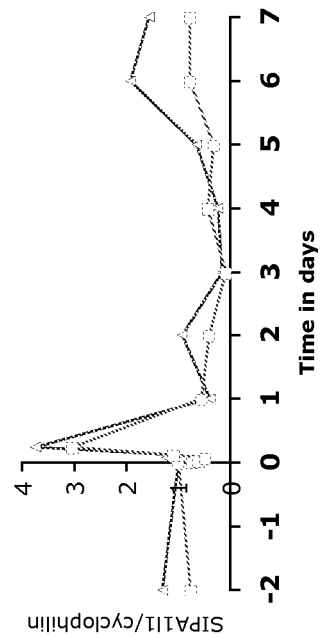

The next step was to determine whether Sipa1l1 gene is conserved among species. To address this question, a RT-PCR was performed on human adipose tissue samples. Preadipocytes and adipocytes were isolated from SCAT or VAT. Isolated preadipocytes were induced to differentiate in vitro until day 7. Results showed that Sipa1l1 is indeed expressed in human fat (FIG. 2D).They indicate that these genes are present in human adipose tissues. Altogether these results suggest that Sipa1l1 is a relevant candidate gene for adipocytes development, possibly required for adipogenesis or fat tissue enlargement in obesity.

Example 3

Expression of Selected Genes During 3T3-L1 Differentiation

Figure 2E:
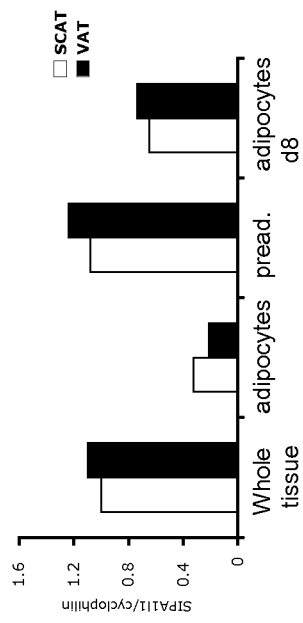

Next, the expression of Sipa1l1 gene was assessed during adipogenesis. For that purpose, mRNA levels were measured by RT-PCR during a detailed differentiation time-course of 3T3-L1 (an adipogenic cell line) (FIG. 2E). The experiment showed that Sipa1l1 is markedly increased in early step (1 to 3 hours after DMI treatment). This pattern is interesting since known adipogenic transcription factors such as CEBP β and γ (Rosen E. D., 2000) Krox20 (Chen Z., 2005) and Ebf (Jimenez M., 2007) show similar expression, suggesting the involvement of this gene in the early steps of adipogenesis.

Example 4 shRNA Knockdown of Sipa1l1 in 3T3-L1 Cells Reduces Adipogenesis

For the loss-of-function studies, shRNA specific for Sipa1l1 subcloned into a retroviral vector from Clontech were used (RNAi-Ready pSIREN-RetroQ ZsGreen or pSIREN). This plasmid contains a GFP marker, which allows controlling the infection efficiency in 3T3-L1 cells. Two different shRNA for Sipa1l1, were cloned into the pSIREN plasmid, and were first tested in 293T HEK cells. This experiment demonstrated the ability of shRNA specific for Sipa1l1 to inhibit Sipa1l1 expression and obtained 95% and 77% of knockdown with shSipa1l1 (FIG. 3A). Both shRNA were thus used for transduction into 3T3-L1 cells.

Figure 3C:
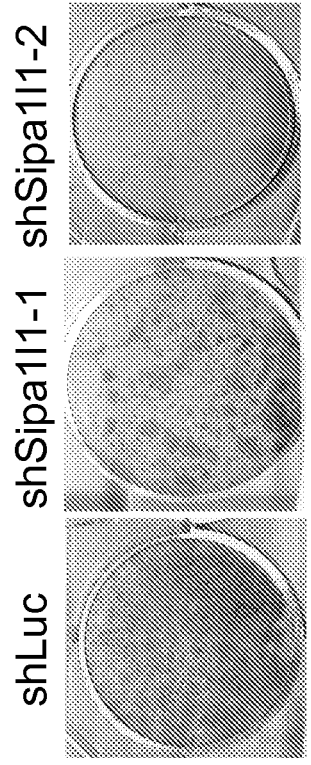
FIG. 3: Knockdown of Sipa1l1 expression and activity by shRNA A) shRNA transfection into 293T cells. pSIREN retroviral plasmids containing shRNA sequences against Sipa1l1 were co-transfected with pCMVSPORT expressing plasmid. As a control for shRNA construct, we used a shRNA against the firefly luciferase protein (shRNA luciferase). 2 shRNA were tested for Sipa1l1 and 77 to 95% of knockdowns were obtained. B) 3T3-L1 cells were transduced with retroviruses containing shRNA directed against luciferase (shLuc) or Sipa1l1 (shSipa1l1). mRNA levels were measured by RT-PCR prior differentiation. We obtained 40% knockdown with both shRNA. C) Oil-red-O pictures of differentiated 3T3-L1 at day 9. Knockdown of Sipa1l1 reduces adipogenesis. D) aP2 (marker of differentiation) mRNA expression measured by RT-PCR in the same cells as in C) at day 9. Results are expressed as mean±sd *P<0.05, , P<0.01; *, P<0.005. n=3.
Figure 3D:
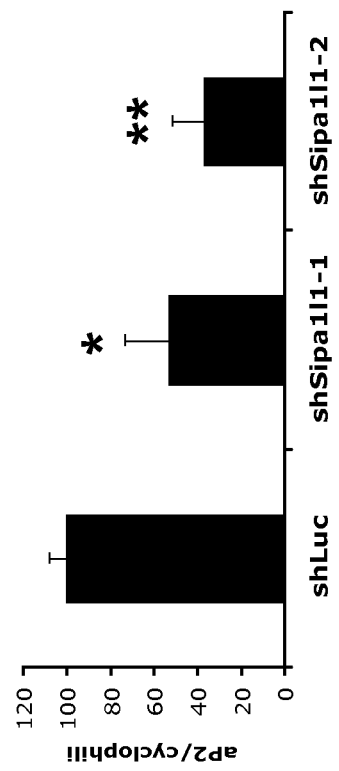

3T3-L1 cells were then infected for 6 hours with retroviral vectors expressing shRNA directed towards either Sipa1l1 (shSipa1l1) or luciferase (shLuc). Using the GFP marker, we observed 90% infection in the 3T3-L1 cells. At day 0, a 60% knockdown for Sipa1l1 was obtained in cells infected with sSipa1l1 (FIG. 3B) whereas no inhibition was obtained with shLuc control. Then, cells were allowed to reach confluence and after one week differentiated with DMI. After 7 to 10 days of differentiation, cells were stained to determine the amount of lipid content with oil-red-O staining. Knockdown of Sipa1l1 reduces adipogenesis as shown by the decrease of lipid staining and marker of adipogenesis in cells transduced with shSipa1l1 compared to control cells transduced with shLuc (FIGS. 3C and 3D).

BIBLIOGRAPHY

Banerjee, S. S., M. W. Feinberg, M. Watanabe, S. Gray, R. L. Haspel, D. J. Denkinger, R. Kawahara, H. Hauner, and M. K. Jain. 2003. The Kruppel-like factor KLF2 inhibits peroxisome proliferator-activated receptor-gamma expression and adipogenesis. J Biol. Chem. 278:2581-4. Epub 2002 Nov. 7.

Chen, Z., J. I. Torrens, A. Anand, B. M. Spiegelman, and J. M. Friedman. 2005. Krox20 stimulates adipogenesis via C/EBPbeta-dependent and -independent Gray, S., M. W. Feinberg, S. Hull, C. T. Kuo, M. Watanabe, S. Sen-Banerjee, A. DePina, R. Haspel, and M. K. Jain. 2002. The Kruppel-like factor KLF15 regulates the insulin-sensitive glucose transporter GLUT4. J Biol Chem 277:34322-8.

Jimenez, M. A., P. Akerblad, M. Sigvardsson, and E. D. Rosen. 2007. Critical role for Ebf1 and Ebf2 in the adipogenic transcriptional cascade. Mol Cell Biol 27: 743-57.

Kang, S., C. N. Bennett, I. Gerin, L. A. Rapp, K. D. Hankenson, and O. A. Macdougald. 2007. Wnt signaling stimulates osteoblastogenesis of mesenchymal precursors by suppressing CCAAT/enhancer-binding protein alpha and peroxisome proliferator-activated receptor gamma. J Biol Chem 282: 14515-24.

Rosen E D, MacDougald O A. 2006. Adipocyte differentiation from the inside out. Nat Rev Mol Cell Biol. 2006 December; 7(12): 885-96.

Rosen E D, Spiegelman B M. Adipocytes as regulators of energy balance and glucose homeostasis. Nature. 2006 Dec. 14; 444(7121): 847-53

Rosen, E. D., C. H. Hsu, X. Wang, S. Sakai, M. W. Freeman, F. J. Gonzalez, and B. M. Spiegelman. 2002. C/EBPalpha induces adipogenesis through PPARgamma: a unified pathway. Genes Dev 16: 22-6.

Tsai, I. C., J. D. Amack, Z. H. Gao, V. Band, H. J. Yost, and D. M. Virshup. 2007. A Wnt-CKIvarepsilon-Rapt pathway regulates gastrulation by modulating SIPA1L1, a Rap GTPase activating protein. Dev Cell 12: 335-47.

Collins S, Martin T L, Surwit R S, Robidoux J. 2004 Genetic vulnerability to diet-induced obesity in the C57BL/6J mouse: physiological and molecular characteristics. Physiol Behav. 81(2):243-8

Jordan M, Wurm F. 2004. Transfection of adherent and suspended cells by calcium phosphate. Methods. 33(2):136-43.

Poirier B, Bidouard J P, Cadrouvele C, Marniquet X, Staels B, O'Connor S E, Janiak P, Herbert J M. 2005. The anti-obesity effect of rimonabant is associated with an improved serum lipid profile. Diabetes Obes Metab. 7(1): 65-72.

Rosen E D, Walkey C J, Puigserver P, Spiegelman B M. 2000. Transcriptional regulation of adipogenesis. Genes Dev. 14(11):1293-307.

The invention claimed is:

1. A method of modulating adipogenesis, comprising administering to a patient in need thereof an inhibitor of Sipa1l1 activity.

2. The method according to claim 1 wherein said inhibitor is administered locally to a target tissue.

3. The method according to claim 1 wherein said inhibitor is administered with at least one pharmaceutically acceptable excipient as a therapeutic for the treatment of obesity and related disorders.

4. The method according to claim 1 or 3, wherein said modulation of adipogenesis results in reduction of visceral or subcutaneous fat accumulation or both.

5. The method of claim 1 wherein said inhibitor is a small nucleic acid molecule selected from the groups consisting of short interfering nucleic acid (siNA), short interfering RNA (siRNA), double-stranded RNA (dsRNA), micro-RNA (miRNA), short hairpin RNA (shRNA) molecules, and combination thereof.

6. The method of claim 1 wherein said inhibitor is a double stranded nucleic acid molecule capable of mediating RNA interference against Sipa1l1 gene expression.

7. The method according to claim 6 wherein the double stranded nucleic acid molecule is a shRNA having sequence SEQ ID NO. 5 or SEQ ID NO. 6.

8. A nucleic acid having sequence SEQ ID NO. 5 or SEQ ID NO. 6.

9. The method according to claim 6 wherein the double stranded nucleic acid molecule is a siRNA having sequence SEQ ID NO. 5 or SEQ ID NO. 6.

* * * * *